(12) United States Patent
Bais et al.

(10) Patent No.: US 8,697,603 B2
(45) Date of Patent: Apr. 15, 2014

(54) COMPOSITIONS AND METHODS FOR INCREASING BIOMASS, IRON CONCENTRATION, AND TOLERANCE TO PATHOGENS IN PLANTS

(71) Applicant: University of Delaware, Newark, DE (US)

(72) Inventors: Harsh Bais, Newark, DE (US); Darla Janine Sherrier, Hockessin, DE (US); Venkatachalam Lakshmanan, Newark, DE (US)

(73) Assignee: University of Delaware, Newark, DE (US)

( * ) Notice: Subject to any disclaimer, the term of this patent is extended or adjusted under 35 U.S.C. 154(b) by 0 days.

(21) Appl. No.: 13/687,339

(22) Filed: Nov. 28, 2012

(65) Prior Publication Data
US 2013/0184150 A1 Jul. 18, 2013

Related U.S. Application Data

(63) Continuation of application No. 13/037,880, filed on Mar. 1, 2011, now abandoned.

(60) Provisional application No. 61/309,134, filed on Mar. 1, 2010, provisional application No. 61/414,108, filed on Nov. 16, 2010, provisional application No. 61/416,039, filed on Nov. 22, 2010.

(51) Int. Cl.
*A01N 25/26* (2006.01)
*A01N 63/00* (2006.01)

(52) U.S. Cl.
USPC .......................................... 504/100; 504/117

(58) Field of Classification Search
None
See application file for complete search history.

(56) References Cited

U.S. PATENT DOCUMENTS

| | | | |
|---|---|---|---|
| 5,809,693 | A | 9/1998 | Chet |
| 6,896,883 | B2 | 5/2005 | Bergstrom et al. |
| 7,632,493 | B2 | 12/2009 | Tzeng et al. |
| 8,318,636 | B2 | 11/2012 | Bais et al. |
| 2003/0228679 | A1 | 12/2003 | Smith et al. |
| 2004/0097372 | A1 | 5/2004 | Abraham et al. |
| 2008/0274528 | A1 | 11/2008 | Dixon |
| 2010/0093538 | A1 | 4/2010 | Gnanamanickam |
| 2010/0260735 | A1* | 10/2010 | Bais et al. ............... 424/93.462 |
| 2011/0212835 | A1 | 9/2011 | Bais |

FOREIGN PATENT DOCUMENTS

| | | |
|---|---|---|
| JP | 10-004954 A | 1/1998 |
| WO | WO 95/20040 A1 | 7/1995 |
| WO | WO 03/020038 A1 | 3/2003 |
| WO | WO 2011/109395 A2 | 9/2011 |
| WO | WO 2011/109395 A3 | 2/2012 |
| WO | WO 2012/067668 A1 | 5/2012 |

OTHER PUBLICATIONS

Rudrappa et al. Root-Secreted Malic Acid Recruits Benefical Soil Bacterial, Plant Physiology, Nov. 2008, vol. 148, pp. 1547-1556).*
Badri et al., "Regulation and function of root exudates," *Plant, Cell and Environment*, Jun. 2009; 32(6):666-681.
Bais et al., "Biocontrol of *Bacillus subtilis* against Infection of *Arabidopsis* Roots by *Pseudomonas syringae* is Facilitated by Biofilm Formation and Surfactin Production," *Plant Physiology*, Jan. 2004; 134:307-319. Made available online Dec. 18, 2003.
Bais, Harsh, "Root Secreted Chemical Mediation in Beneficial Plant-Microbe Interactions," Grant Abstract, Grant Number Grant 0814477 [online]. Division of Integrative Organismal Systems, National Science Foundation, project dates Aug. 15, 2008 to Jan. 31, 2012 [retrieved on Aug. 21, 2013]. Retrieved from the Internet: <www.nsf.gov/awardsearch/showAward?AWD_ID=0814477 &HistoricalAwards=false>; 2 pages.
Bais, Harsh, "The Effect of the Microbiome on the Rice Transcriptome," Grant Abstract, Grant Number Grant 0923806 [online]. Division of Mocelcular and Cellular Biosciences, National Science Foundation, project dates Sep. 1, 2009 to Aug. 31, 2014 [retrieved on Aug. 21, 2013]. Retrieved from the Internet: <www.nsf.gov/awardsearch/showAward?AWD_ID=0923806 &HistoricalAwards=false>; 2 pages.
Cavaglieri et al., "Biocontrol of *Bacillus subtilis* Against *Fusarium verticillioides* In Vitro and At the Maize Root Level," *Research in Microbiology*, Jun.-Jul. 2005; 156:748-754.
Chapman, "A little collaboration grows a long way," Oct. 2010 *University of Delaware Research: Eco-Innovation* vol. 2/No. 1; cover page, table contents, and p. 6. Available on the Internet: <http://www.udel.edu/researchmagazineissue/vol2_no1_enviro/daretobefirst.html#dare2>.

(Continued)

*Primary Examiner* — Alton Pryor
(74) *Attorney, Agent, or Firm* — Mueting, Raasch & Gebhardt, P.A.

(57) ABSTRACT

Methods for producing greater biomass in a plant, increasing the drought tolerance of a plant, producing a decreased lignin concentration in a plant, producing a greater iron concentration in a plant, or inhibiting fungal infection in a plant comprise administering *Bacillus subtilis* FB17 to the plant, the seed of the plant, or soil surrounding the plant or the seed in an amount effective to produce greater biomass, increase the drought tolerance, produce a decreased lignin concentration, produce a greater iron concentration, or inhibit fungal infection in the plant compared to an untreated plant, respectively. Agricultural carriers and seed coatings comprising *Bacillus subtilis* FB17 are provided. The biomass of a plant which has been administered *Bacillus subtilis* FB17 can be converted to a biofuel or can be used as a food crop or in other uses.

24 Claims, 23 Drawing Sheets

(56) References Cited

OTHER PUBLICATIONS

Chapman, "Innovation on the rise," Oct. 2010 *University of Delaware Research: Eco-Innovation* vol. 2/No. 1; cover page, table contents, and p. 7. Available on the Internet: <http://www.udel.edu/researchmagazine/issue/vol2_no1_enviro/daretobefirst.html#dare2>.

Choudhary et al., "Interactions of *Bacillus* spp. and plants—With special reference to induced systemic resistance (ISR)," *Microbiological Research*, 2009; 164(5):493-513. Made available online Oct. 8, 2008.

Fall et al., "A Simple Method to Isolate Biofilm-Forming *Bacillus subtilis* and Related Species From Plant Roots," *Systematic and Applied Microbiology*, 2004; 27:372-379.

Gordillo et al., "Motility and Chemotaxis of *Pseudomonas* sp. B4 Towards Polychlorobiphenyls and Chlorobenzoates," *FEMS Microbiol Ecol.*, 2007; 60:322-328.

Heil et al., "Fitness Costs of Induced Resistance: Emerging Experimental Support for a Slippery Concept," *Trends in Plant Science*, Feb. 2002; 7(2):61-67.

Hoekenga et al., "AtALMT1, Which Encodes a Malate Transporter, Is Identified As One of Several Genes Critical for Aluminum Tolerance in Arabidopsis," *PNAS*, 2006; 103(25):9738-9743.

Katagiri et al., "The *Arabidopsis thaliana-Pseudomonas* Syringae Interaction," *American Society of Plant Biologists*, The *Arabidopsis* Book, First Published on Mar. 27, 2002; doi:10.1199/tab.0039: 1-35.

Khalid, "Screening Plant Growth-Promoting Rhizobacteria for Improving Growth and Yield of Wheat," *Journal of Applied Microbiology*, 2004; 96:473-480.

Kobayashi et al., "Characterization of AtALMT1 Expression in Aluminum-Inducible Malate Release and Its Role for Rhizotoxic Stress Tolerance in *Arabidopsis*," *Plant Physiology*, 2007; 145:843-852.

Kokalis-Burelle et al., "Plant growth-promoting rhizobacteria as transplant amendments and their effects on indigenous rhizosphere microorganisms," *Applied Soil Ecology*, 2006; 31:91-100.

Kumar et al., "Rhizobacteria *Bacillus subtilis* restricts foliar pathogen entry through stomata," Nov. 2012 Plant J. 74:694-706. Available online on Sep. 24, 2012.

Lucy, "Applications of Free Living Plant Growth-promoting Rhizobacteria," *Antonie van Leeuwenhoek*, Aug. 2004; 86(2):1-25.

Melotto et al., "Role of stomata in plant innate immunity and foliar bacterial diseases," Sep. 2008 *Annu. Rev. Phytopathol.* 46:101-122. Author manuscript available online.

Pare, Paul, "Natural Product Chemistry and Mechanisms of Flavonoid Oxidation," Grant Abstract, Grant No. D-1478 [online]. The Welch Foundation, project dates unknown [retrieved on Jan. 15, 2013]. 2011 Annual Report and Supplement (including abstract D-1478) retrieved from the Internet: <http://www.welch1.org/newsroom-and-reports>; cover page, and pp. 12 and 79.

Ramos et al., "Fermentative Metabolism of *Bacillus subtilis*: Physiology and Regulation of Gene Expression," *Journal of Bacteriology*, Jun. 2000; 182(11):3072-3080.

"Recruit," in *Merriam-Webster Dictionary*. Available online [retrieved on Jan. 25, 2013]. Retrieved from the Internet: <http://www.merriam-webster.com/dictionary/recruit>; 1 pg.

Rudrappa et al., "A Degradation Product of the Salicylic Acid Pathway Triggers Oxidative Stress Resulting in Down-Regulation of *Bacillus subtilis* Biofilm Formation on *Arabidopsis thaliana* roots," *Planta*, Jul. 2007; 226:283-297.

Rudrappa et al., "Causes and Consequences of Plant-Associated Biofilms," *FEMS Microbiol Ecol.*, May 2008; 64:153-166.

Rudrappa et al., "Root-Secreted Malic Acid Recruits Beneficial Soil Bacteria," *Plant Physiology*, Nov. 2008; 148(3):1547-1556. Available online Sep. 26, 2008.

Rudrappa et al., Supplemental Data for "Root-Secreted Malic Acid Recruits Beneficial Soil Bacteria," *Plant Physiology*, Nov. 2008; 148(3):1547-1556, 4 pgs., epub date Sep. 26, 2008.

Rudrappa et al., Abstract for "The rhizobacterial elicitor acetoin induces systemic resistance in *Arabidopsis thaliana*," Mar./Apr. 2010 *Communicative & Integrative Biology* 3(2). Available on Nov. 9, 2009.

Rudrappa et al., "The rhizobacterial elicitor acetoin induces systemic resistance in *Arabidopsis thaliana*," Mar./Apr. 2010 *Communicative & Integrative Biology* 3(2):130-138. Submitted on Jul. 9, 2009; revised and accepted on Nov. 9, 2009. Available online Feb. 2, 2010.

Ryu et al., Bacterial Volatiles Promote Growth in *Arabidopsis*, Proceedings of the National Academy of Sciences of the United States of America, vol. 100, No. 8 (2003), pp. 4927-4932.

Ryu et al., "Bacterial Volatiles Induce Systemic Resistance in Arabidopsis," *American Society of Plant Biologists, Plant Physiology*, Mar. 2004; 134(3):1017-1026. Made available online Feb. 2004.

Schisler, "Formulation of *Bacillus* Spp. for Biological Control of Plant Disease," *Phytopathology*, Nov. 2004; 94(11):127-1271.

Scott et al., "Salicylate Accumulation Inhibits Growth at Chilling Temperature in *Arabidopsis*," The American Society of Plant Biologists, *Plant Physiology*, 2004; 135:1040-1049.

Sticklen, "Plant Genetic Engineering for Biofuel Production: Towards Affordable Cellulosic Ethanol," *Nature Reviews: Genetics*, Jun. 2008; 9(6):433-443.

Yang et al., "Rhizosphere Bacteria Help Plants Tolerate Abiotic Stress," *Trends in Plant Science*, Jan. 2009; 14(1):1-4. Available online Dec. 4, 2008.

Zhao et al., "Virulence systems of *Pseudomonas syringae* pv. tomato promote bacterial speck disease in tomato by targeting the jasmonate signaling pathway," *The Plant Journal*, Dec. 2003; 36(4):485-499.

International Search Report for International Patent Application Serial No. PCT/US2011/026683, filed Mar. 1, 2011; 6 pgs, mailed Dec. 15, 2011.

Written Opinion for International Patent Application Serial No. PCT/US2011/026683, filed Mar. 1, 2011; 6 pgs, mailed Dec. 15, 2011.

International Preliminary Report on Patentability for International Application Serial No. PCT/US2011/026683, filed Mar. 1, 2011; 7 pgs, issued Sep. 4, 2012.

International Search Report for International Patent Application No. PCT/US2011/026693, filed Mar. 1, 2011; 3 pgs, mailed Jan. 2, 2012.

Written Opinion for International Patent Application No. PCT/US2011/026693, filed Mar. 1, 2011; 3 pgs, mailed Jan. 2, 2012.

International Preliminary Report on Patentability for International Application Serial No. PCT/US2011/026693, filed Mar. 1, 2011; 4 pgs, issued May 21, 2013.

Office Action for U.S. Appl. No. 12/758,361, filed Apr. 12, 2010; 6 pgs, issued Sep. 26, 2012.

Supplemental Amendment filed Feb. 26, 2013, for U.S. Appl. No. 12/758,361, filed Apr. 12, 2010; 12 pgs.

Second Supplemental Amendment filed Mar. 22, 2013, for U.S. Appl. No. 12/758,361, filed Apr. 12, 2010; 7 pgs.

Office Action for U.S. Appl. No. 13/037,880, filed Mar. 1, 2011; 9 pgs. issued Mar. 7, 2012.

Amendment and Response filed Jun. 6, 2012, for U.S. Appl. No. 13/037,880, filed Mar. 1, 2011; 13 pgs.

Office Action for U.S. Appl. No. 13/037,880, filed Mar. 1, 2011; 11 pgs, issued Jun. 28, 2012.

* cited by examiner

| Trait | Zea mays Field Corn | Zea mays CML10 Exotic Corn | Zea mays CML258 Exotic Corn | Glycine max | Solanum lycopersicum Roma Tomato | Other | Rice | Arabidopsis | Brachypodium | Zinnia | Barley |
|---|---|---|---|---|---|---|---|---|---|---|---|
| Enhanced Germination | | | | | √ | | | | | | |
| Faster Growth Rate | √ | √ | √ | | | | | | | | |
| Higher Biomass | √ | | | | | | | | √ | | |
| Higher Yield at Harvest | √ | | | | | | | | | | |
| Enhanced Nutritional Properties | | | | | | | √ | | | | |
| Decreased Lignin Content | √ | | | | | | | | | | |
| Enhanced Drought Protection | √ | | | | | √ | | √ | √ | | |
| Antifungal Properties | | | | | | √ | √ | | | | |
| Increased Vigor | | | | √ | | | √ | | | | |
| Increased Total Chlorophyll | √ | √ | | | √ | | | | | | |
| Increased Total Carotenoid | | √ | √ | | √ | | | | | √ | √ |
| Photosynthetic Efficiency | | | | | | | | | √ | | |

FIG. 23

COMPOSITIONS AND METHODS FOR INCREASING BIOMASS, IRON CONCENTRATION, AND TOLERANCE TO PATHOGENS IN PLANTS

CROSS-REFERENCE TO RELATED APPLICATIONS

This application is a continuation of U.S. application Ser. No. 13/037,880, filed Mar. 1, 2011, which claims the benefit of application Ser. No. 61/309,134, filed Mar. 1, 2010, application Ser. No. 61/414,108, filed Nov. 16, 2010, and application Ser. No. 61/416,039, filed Nov. 22, 2010, which are incorporated herein by reference in their entirety and for all purposes.

STATEMENT OF GOVERNMENT SUPPORT

This invention was made with government support under Grant No. 0923806 and Grant No. IOS-0814477 awarded by the National Science Foundation. The government has certain rights in this invention.

FIELD OF THE INVENTION

This invention relates generally to the use of plant growth promoting rhizobacteria to enhance various characteristics of plant growth, including increasing biomass, increasing drought tolerance, decreasing lignin content, increasing seed germination, increasing iron concentration, and increasing tolerance to pathogens. In particular, embodiments of the present invention relate to the administration of *Bacillus subtilis* FB17 to plants. The resulting plants can be used in the production of biofuels, food, or for other purposes.

BACKGROUND OF THE INVENTION

Food security has always been a top priority throughout the world, and an escalating concern for the environmental impact of crop production necessitates the development and use of novel methods to enhance productivity while protecting the environment Plant biologists develop and implement strategies for efficient production of crop plants with the aim of ensuring the availability of essential raw materials to the world's growing population. However, the development of biofuel and renewable technologies adds to this challenge since they have also become an increasingly important priority. Therefore, there is an increased need for improved approaches to enhance crop yield in diverse field conditions.

The multitude of different geographic environments and climates throughout the world present different types of challenges in generating increased biomass and yield potential in crop plants. Drought is a major factor which limits crop production globally. Long-term drought or short-term drought in the growing season can severely limit or even eliminate crop production. Changes in global weather patterns have affected the frequency and intensity of drought, even in prime cropping regions of the world.

Nutrient availability also limits crop production. Soil augmentation with nutrients is costly and energy intensive, and even when nutrients are available in sufficient quantities, crop plants are sometimes inefficient at nutrient uptake. Poor uptake of essential nutrients results in lower yields and food crops with lower nutritional values. For example, rice (the seed of the monocot plants *Oryza sativa* or *Oryza glaberrima*) is the most important staple food for over two-thirds the world's population, providing a significant proportion of the calories consumed. Since rice is the main staple food for much of the global population, producing rice with higher levels of iron can have a major impact on reducing micronutrient malnutrition throughout the world, as iron deficiency is one of the most widespread micronutrient deficiencies in humans worldwide.

Pathogen stress also limits productivity. Plants must invest energy to survive pathogen attack, and this diversion of energy results in lower yields. Plants also modify their composition to restrict disease progression, and these changes often make crop processing more difficult. Further, some crop pathogens cannot be limited effectively by genetic diversity, nor chemical control, and have significant impact on crop production globally.

Rice blast (*Magnaporthe grisea* or *Magnaporthe oryzae*) is a plant-pathogenic fungus that causes a serious disease affecting rice. It causes economically significant crop losses annually, contributing to an estimated 40% in crop yield. Rice blast destroys enough rice to feed millions of people throughout the world every growth season. Since rice is an important food staple for much of the world, the effects of rice blast have a broad impact on human health and the environment. Rice shortfalls contribute directly to human starvation. The rice blast further contributes to crop loss and requires the use of additional resources to compensate for reduced yield. There continues to be a great need for strategies that enhance various characteristics of plant growth in diverse growing conditions, such as tolerance to drought stress, tolerance to pathogen pressure, nutrient availability, and ultimately crop yield, so that greater amounts of food with increased nutrition can be available to the global population, and for other important benefits, such as biofuel production.

SUMMARY OF THE INVENTION

An embodiment of the present invention provides a method for producing a greater biomass in a plant comprising administering *Bacillus subtilis* FB17 to the plant, plant seed, or soil surrounding the plant or plant seed in an amount effective to produce a greater biomass in the plant compared to an untreated plant.

Another embodiment provides a method for increasing the drought tolerance of a plant comprising administering *Bacillus subtilis* FB17 to the plant, plant seed, or soil surrounding the plant or plant seed in an amount effective to increase the drought tolerance of the plant compared to an untreated plant.

Another embodiment provides a method for producing a decreased lignin concentration in a plant comprising administering *Bacillus subtilis* FB17 to the plant, plant seed, or soil surrounding the plant or plant seed in an amount effective to produce a decreased lignin concentration in the plant compared to an untreated plant.

Another embodiment provides a method for increasing the seed germination in plants comprising administering *Bacillus subtilis* FB17 to the plants, plant seeds, or soil surrounding the plants or plant seeds in an amount effective to increase the seed germination of the plants compared to untreated plants.

Another embodiment provides a method for producing a greater iron concentration in a plant, particularly a rice plant, comprising administering *Bacillus subtilis* FB17 to the plant, the seed of the plant, or soil surrounding the plant or the seed in an amount effective to produce a greater iron concentration in the plant compared to an untreated plant.

Another embodiment provides a method for inhibiting growth of a plant fungal pathogen and infection of a plant, particularly a rice plant, by a fungal pathogen, particularly rice blast, comprising administering *Bacillus subtilis* FB17 to the plant, the seed of the plant, or soil surrounding the plant or the seed in an amount effective to inhibit infection of the plant by the fungal pathogen.

Additional embodiments provide agricultural carriers and seed coatings comprising *Bacillus subtilis* FB17. The biomass of a plant which has been administered *Bacillus subtilis* FB17 can be converted to a biofuel, and the crop produced can be used safely for human or animal foodstock, or for other purposes.

BRIEF DESCRIPTION OF THE FIGURES

FIG. 23: Summary of the effects of *B. subtilis* FB17 on different traits in multiple plant species.

DETAILED DESCRIPTION OF THE INVENTION

The applicants have discovered that a strain of plant growth promoting rhizobacteria (PGPR), *Bacillus subtilis* FB17, exhibits surprising effects when administered to plants. *B. subtilis* strain FB17 was originally isolated from red beet roots in North America (see Fall et al. 2004 *System Appli. Microbiol.* 27: 372-379, incorporated herein by reference). This strain was isolated from beet root on the basis of its ability to form surface biofilm and dendritic growth.

In particular, *Bacillus subtilis* FB17 has provided a surprising enhancement of biomass in phylogenetically diverse plants, as well as increased photosynthetic efficiency and enhanced growth rates in drought conditions. Administration of *Bacillus subtilis* FB17 to plants has also resulted in decreased concentrations of lignin in plants, which can provide important benefits in the field of bioenergy, as lignin is one of the chief barriers in converting plant biomass to biofuel. With respect to rice plants, *Bacillus subtilis* FB17 has provided a surprising enhancement in the iron concentration in rice and has also been shown to attenuate the growth of rice blast, a fungal pathogen that destroys rice crops around the world. The present invention provides methods for increasing biomass, increasing drought tolerance, decreasing lignin content, increasing seed germination, increasing iron concentration, and increasing tolerance to pathogens in various plants, particularly crop plants such as corn, soybean, and rice plants. The present invention also provides agricultural carriers and seed coatings comprising *Bacillus subtilis* FB17.

An embodiment of the present invention provides a method for producing a greater biomass in a plant comprising administering *Bacillus subtilis* FB17 to the plant, the seed of the plant, or soil surrounding the plant or the seed in an amount effective to produce a greater biomass in the plant compared to an untreated plant. As used herein, the biomass in a plant refers to the total mass of the plant's matter. Unless specified otherwise, biomass comprises both aboveground biomass (i.e., aerial biomass, including but not limited to stem, leaves, and/or grain) and belowground biomass (i.e., roots). The biomass of a plant that has been administered *Bacillus subtilis* FB17 can be measured according to known methods. In one embodiment, the biomass of the plant is measured according to the dry weight (DW) of the plant in grams.

Figure 4:
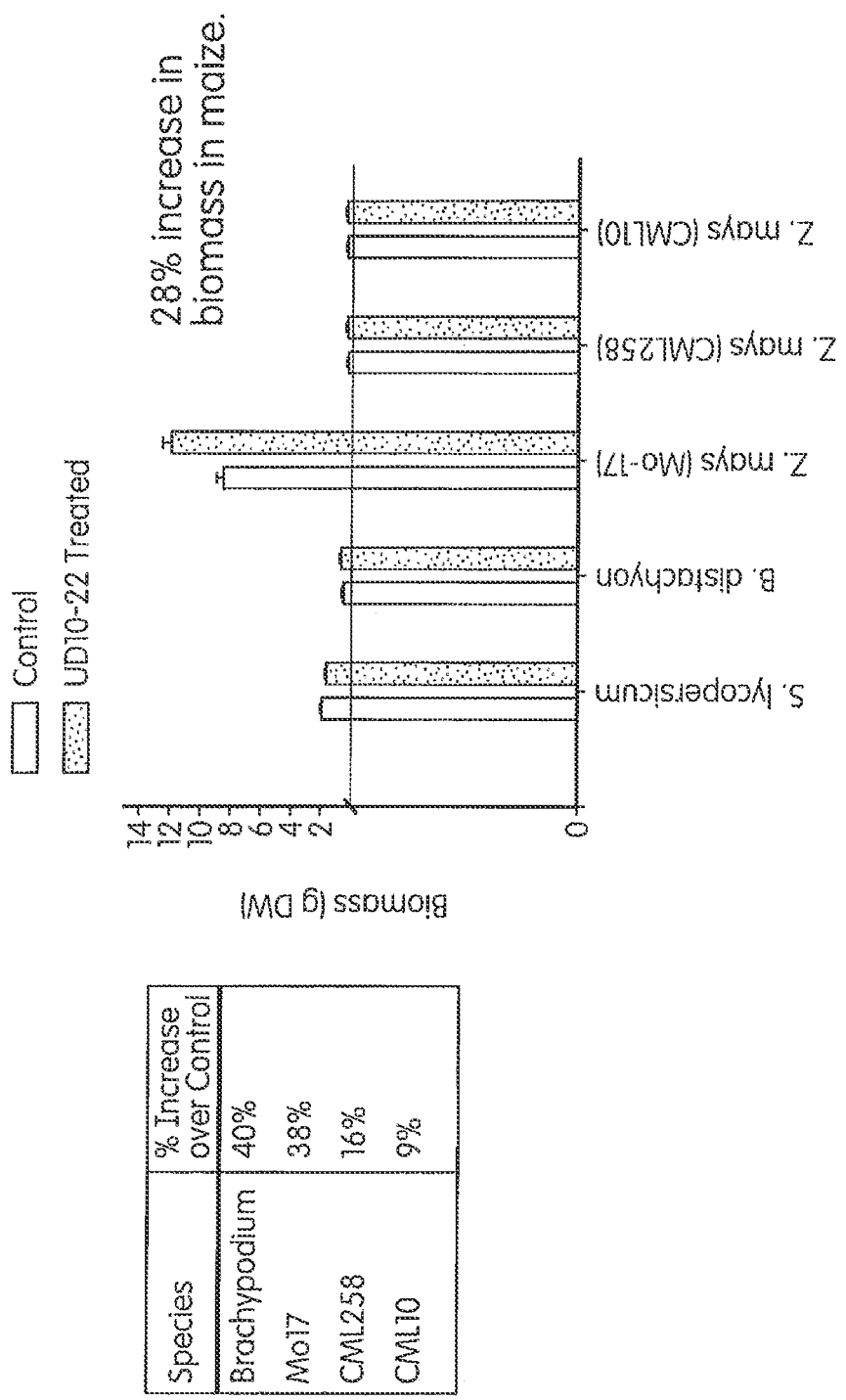
FIG. 4: Total biomass gain in different plant species treated with *B. subtilis* FB17. Significant increase (~28%) in both aerial and root biomass was observed with *Z. mays* (MO17).

The biomass of a plant that has been administered *Bacillus subtilis* FB17 can be measured at a timepoint that is between about 7 days to about 100 days, about 10 days to about 75 days, or about 15 days to about 35 days following administration of *Bacillus subtilis* FB17 to the plant. Alternatively, the biomass of a crop plant that has been administered *Bacillus subtilis* FB17 can be measured at the time that the plant is harvested to collect its grain or produce, i.e., at the time that the mature crop plant such as a corn, soybean, or tomato plant, is gathered from a field. As an example, a crop plant that has been administered *Bacillus subtilis* FB17 according to a method of the present invention produces a greater amount of the total aboveground and belowground biomass as measured in grams of dry weight, in an amount of at least about 1%, between about 5% and about 200%, between about 5% and about 100%, between about 7.5% and about 75%, between about 15% and about 60%, or between about 30% and about 55% greater than an untreated plant. In one embodiment, a method comprises administering *Bacillus subtilis* FB17 to the plant seed prior to planting the seed in soil in an amount effective to produce a greater biomass in the plant in an amount of between about 5% to about 100% greater than an untreated plant, following the administration of *Bacillus subtilis* FB17. For example, as illustrated in FIG. 4, an increase of about 28% in aerial and root biomass was observed in *Bacillus subtilis* FB17 treated corn, compared to untreated corn 15 days post treatment.

Figure 19:
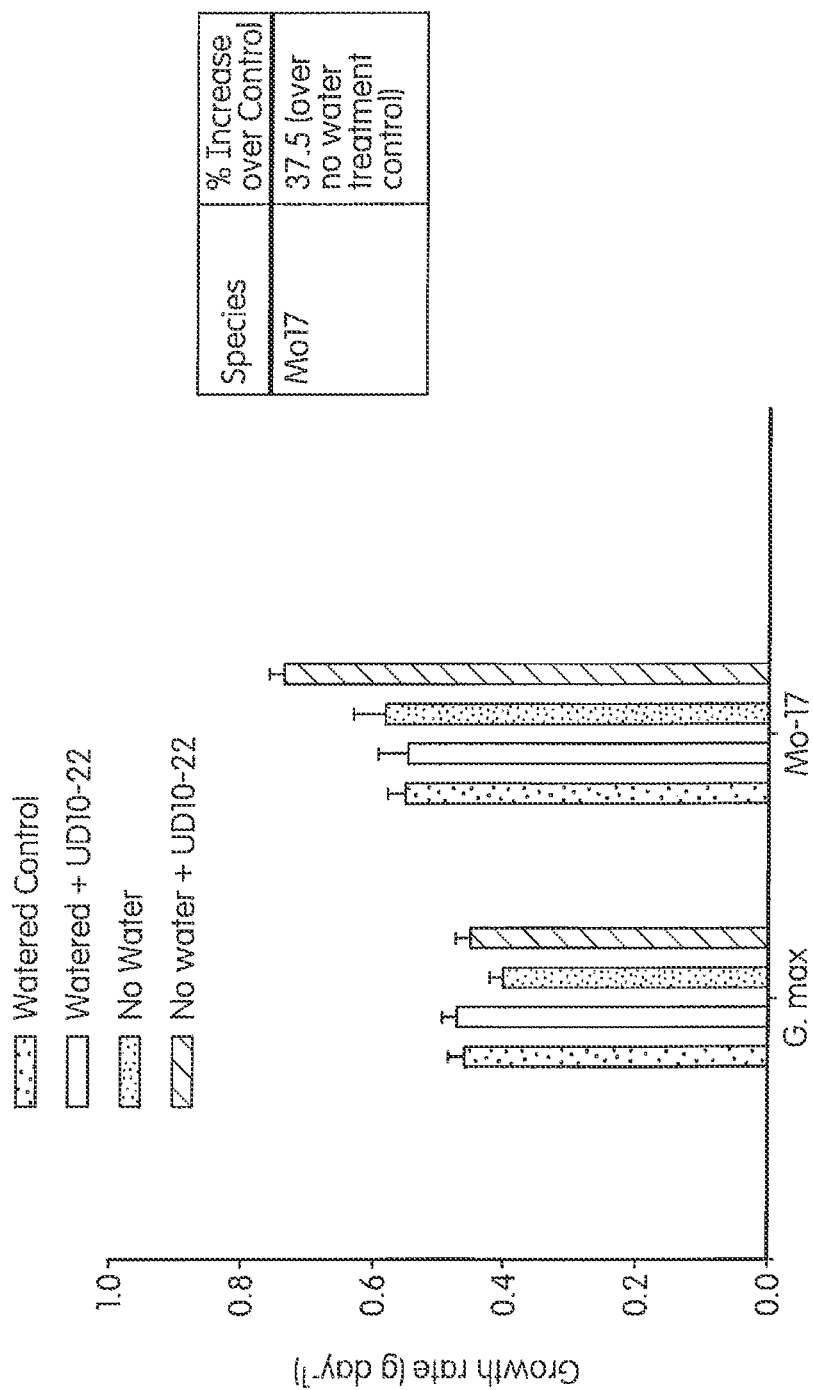
FIG. 19: Drought tolerance in plants treated with *B. subtilis* FB17. Significant increase in growth rate under drought treatments (no water) was observed in MO17, i.e., 37.5% increase over drought stressed (no water) uninoculated treatment control post FB17 treatment

Another embodiment of the present invention provides a method for producing a greater drought tolerance in a plant comprising administering *Bacillus subtilis* FB17 to the plant, the seed of the plant, or soil surrounding the plant or the seed in an amount effective to produce a greater drought tolerance in the plant compared to an untreated plant. A drought is the absence of rainfall or irrigation for a period of time sufficient to deplete soil moisture and injure plants. Drought stress results when water loss from the plant exceeds the ability of the plant's roots to absorb water and when the plant's water content is reduced enough to interfere with normal plant processes. A plant responds to a lack of water by halting growth and reducing photosynthesis and other plant processes in order to reduce water use. As used herein, drought tolerance refers to a plant's growth rate per day in the absence of water, for example, grams per day of biomass increase in a *Bacillus subtilis* FB17 inoculated plant compared to an untreated plant. For example, as illustrated in FIG. 19, corn plants seed treated with *Bacillus subtilis* FB17 in the absence of water produced about 37.5% greater growth rate per day compared to untreated plants 15 days post-treatment. In one embodiment, a method comprises administering *Bacillus subtilis* FB17 to the plant, soil surrounding the plant, or the plant seed prior to planting the seed in soil in an amount effective to produce a greater drought tolerance in the plant in an amount of at least about 10% greater than an untreated plant, following the administration of said *Bacillus subtilis* FB17.

Figure 20:
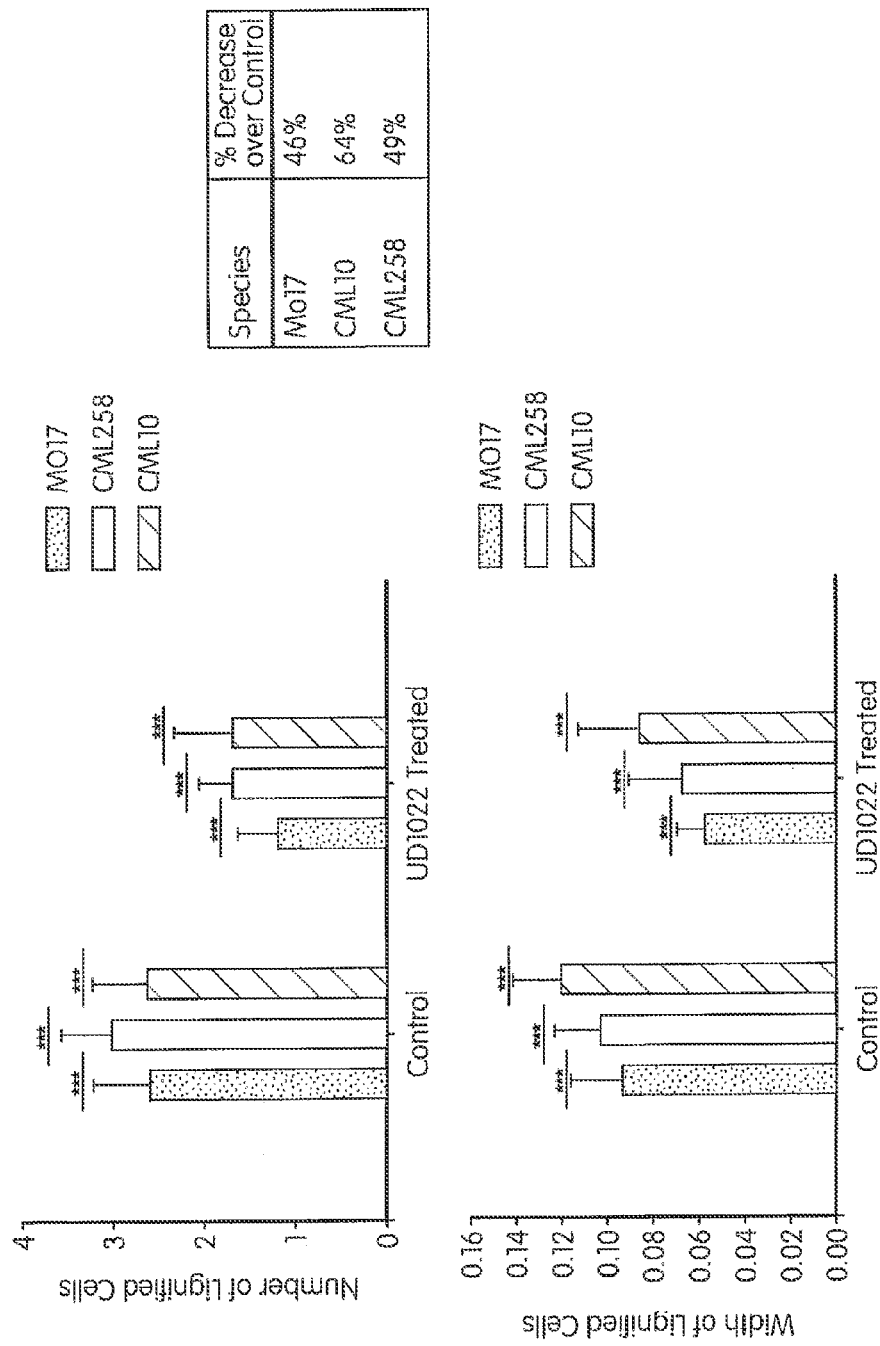
FIG. 20: *B. subtilis* FB17 seed treatment reduces lignin content in corn. Significant reduction of total lignin content was observed in *Z. mays* (MO17=46%; CML10=64% and CML58=49%) post FB17 treatment under no stress conditions.

Another embodiment of the present invention provides a method for producing a decreased lignin concentration in a plant comprising administering *Bacillus subtilis* FB17 to the plant, the seed of the plant, or soil surrounding the plant or the seed in an amount effective to produce a decreased lignin concentration in the plant compared to an untreated plant. The lignin concentration can be measured according to known methods. For example, as illustrated in FIG. 20, plants treated with *Bacillus subtilis* FB17 exhibited between about 46% and about 64% decreases in the number of lignified cells observed in untreated plants. Lignin is an integral component of plants and is found within plant cell walls, as well as between plant cells. Lignin is one of the chief barriers to converting plant biomass to biofuel. Cellulose, another plant component, is currently the main source for biofuels. While cellulose is easily fermented to alcohol, lignin does not convert using existing fermentation processes and renders extraction of fermentable sugars difficult. It is therefore beneficial to produce plants that have decreased concentrations of lignin. The present invention provides biofuels that are produced by converting any of the biomass of a plant (e.g., the entire biomass of the plant or any part of the biomass of the plant) that has been administered *Bacillus subtilis* FB17 according to any of the methods of the present invention to a biofuel. The biomass of a plant that has been administered *Bacillus subtilis* FB17 can be converted to biofuel by any known method, such as by fermentation of the sugar components of the plant.

Figure 16:
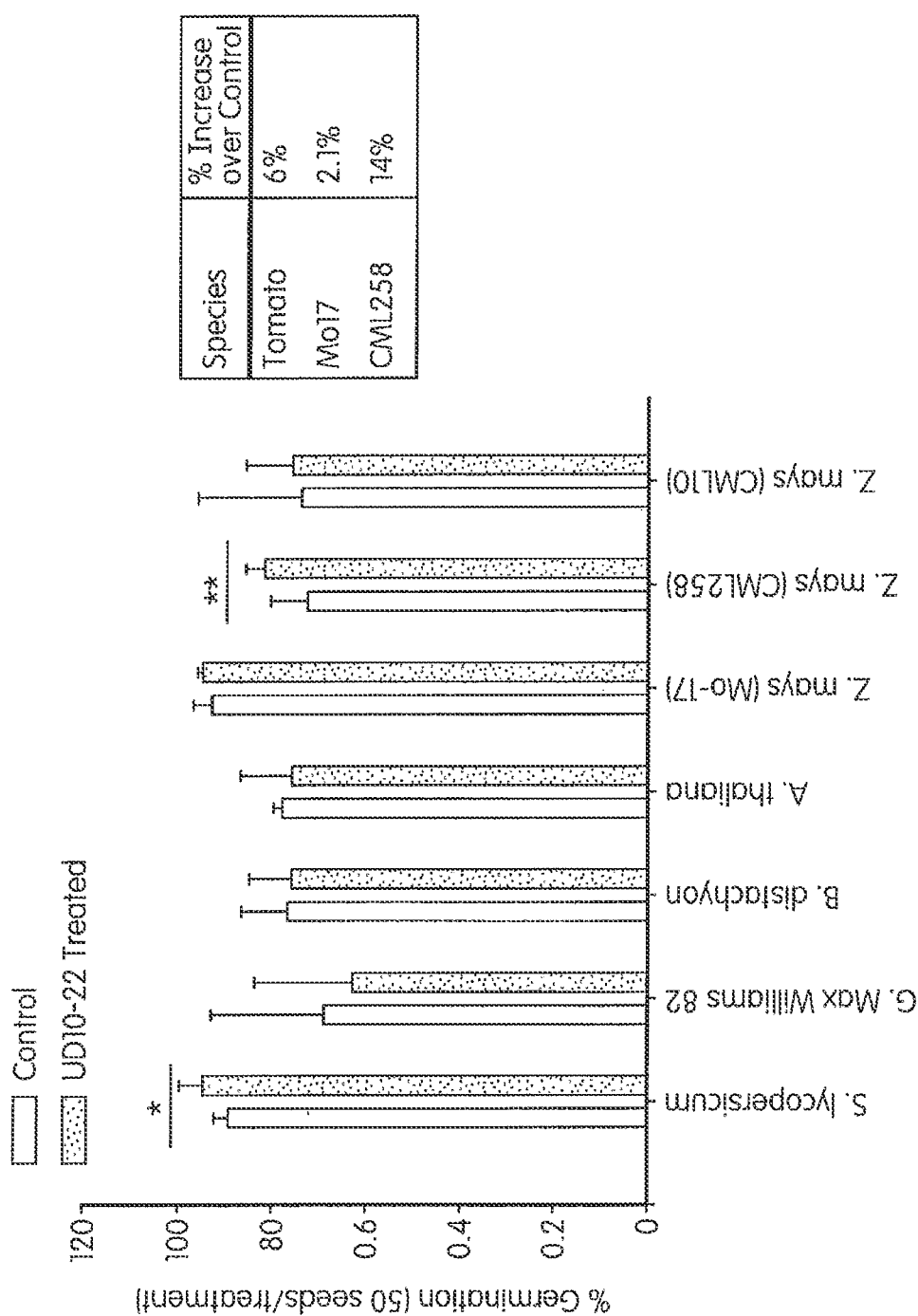
FIG. 16: Percentage germination enhancement in seeds treated with *B. subtilis* FB17. Significant increase in total germination percentage content was observed in tomato (6%), *Z. mays* MO17 (2.1%) and CML258 (14%) post FB17 treatment. Notably, exotic corn line CML258 germination increased dramatically.

Another embodiment of the present invention provides a method for increasing the rate of seed germination in plants comprising administering *Bacillus subtilis* FB17 to the plants, plant seeds, or soil surrounding the plants or plant seeds in an amount effective to increase the seed germination of the plants compared to untreated plants. For example, as illustrated in FIG. 16, increases in total germination percentages were observed in tomato and corn plants following administration with *Bacillus subtilis* FB17.

Figure 22:
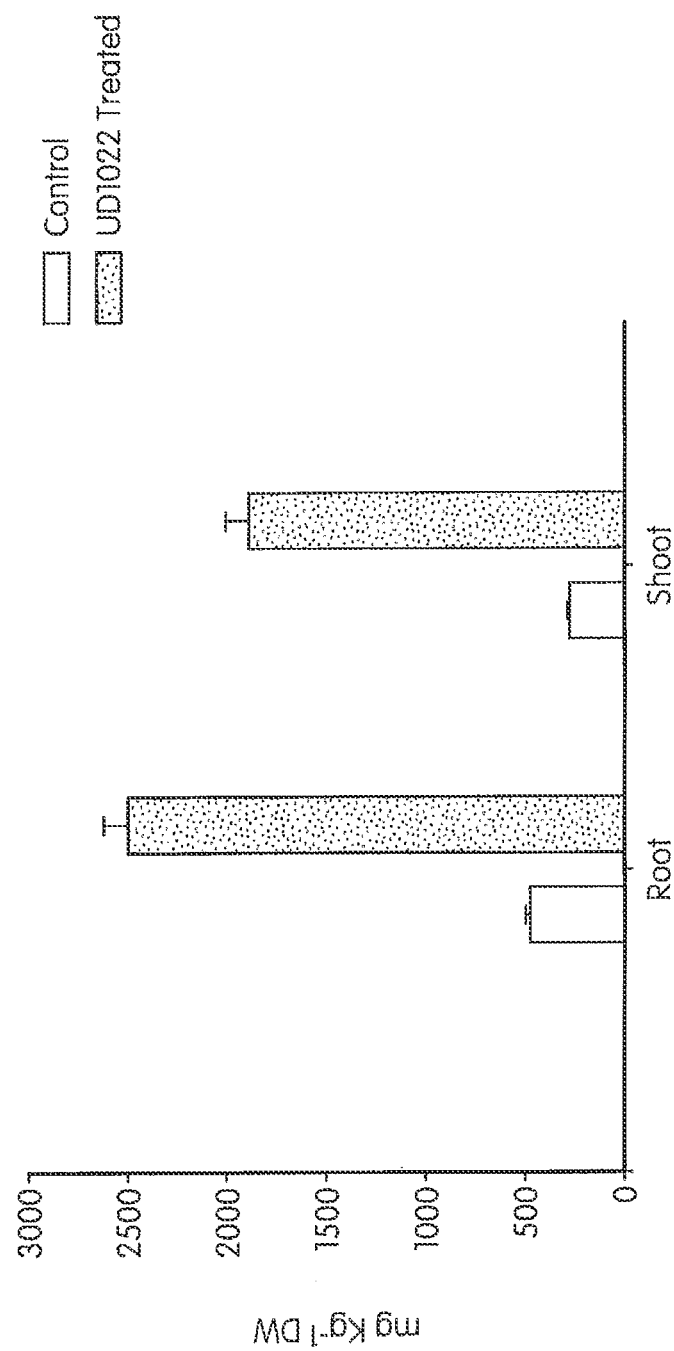
FIG. 22: Iron concentration observed in *Bacillus subtilis* FB17 treated rice plants compared to untreated rice plants. This data shows that inoculation with FB17 results in greater crop yield and higher concentrations of iron in the rice grain.

Another embodiment of the present invention provides a method for producing a greater iron concentration in a plant, particularly a rice plant, comprising administering *Bacillus subtilis* FB17 to the plant, the seed of the plant, or soil surrounding the plant or the seed in an amount effective to produce a greater iron concentration in the plant compared to an untreated plant. As iron deficiency is one of the most widespread micronutrient deficiencies in humans, and rice is the most important staple food for a large part of the world's population, rice plants produced according to methods of the present invention can provide important nutritional benefits throughout the world. The iron concentration of a plant that has been administered *Bacillus subtilis* FB17 can be measured according to known methods, including inductively coupled plasma-atomic emission spectroscopy (ICP-AES), inductively coupled plasma mass spectroscopy (ICP-MS), or other standard methods. In one embodiment, the iron concentration of the plant is measured according to the milligrams of iron per kilogram of the dry weight of the plant. As illustrated in FIG. 22, an approximately 81% increase in iron content was observed in FB17-treated rice plants compared to untreated plants, as measured by mg of iron per kg of dry weight of the plant Suitable rice plants for use in the invention include *Oryza sativa*, *Oryza glaberrima*, and all subspecies and cultivars thereof. The iron concentration of a rice plant that has been administered *Bacillus subtilis* FB17 can be measured at the time that the rice is harvested to collect its grain or produce, i.e., at the time that the mature rice grains are gathered from a field. Alternatively, the iron concentration of a rice plant that has been administered *Bacillus subtilis* FB17 can be measured at a time-point that is between, for example, about one week to about five months, preferably about three months following administration of *Bacillus subtilis* FB17 to the rice plant. A rice plant that has been administered *Bacillus subtilis* FB17 according to a method of the present invention produces a greater amount of iron, as measured, for example, in grams of iron per gram of dry weight of aboveground and belowground biomass of the rice plant.

As an example, a rice plant that has been administered *Bacillus subtilis* FB17 according to a method of the present invention produces a greater amount of iron per aboveground and belowground biomass dry weight of the rice plant, in an amount that is at least about 5%, between about 10% and about 200%, between about 25% and about 150%, between about 50% and about 100%, between about 70% and about 90%, between about 75% and about 85%, or about 80% greater than an untreated plant. For example, in one embodiment, a method comprises administering *Bacillus subtilis* FB17 to a rice seed prior to planting the rice seed in soil in an amount effective to produce a greater iron concentration in the rice plant in an amount of at least about 25% greater than an untreated plant, following the administration of said *Bacillus subtilis* FB17.

Another embodiment of the present invention provides a method for inhibiting infection of a plant by a fungal pathogen comprising administering *Bacillus subtilis* FB17 to the plant, the seed of the plant, or soil surrounding the plant or the seed in an amount effective to inhibit infection of the plant by the fungal pathogen compared to an untreated plant. Examples of plants include rice and barley plants, such as the rice cultivar Nipponbare. In a particular embodiment, the present invention provides methods for inhibiting infection of a rice plant by a fungal pathogen, particularly rice blast, comprising administering *Bacillus subtilis* FB17 to the rice plant, the seed of the rice plant, or soil surrounding the rice plant or the seed in an amount effective to inhibit infection of the rice plant by the fungal pathogen compared to an untreated rice plant. As used herein, "rice blast" refers to the plant-pathogenic fungus *Magnaporthe grisea* or *Magnaporthe oryzae*.

Symptoms of rice blast include lesions or spots (which may be, for example, white or gray) produced on any part of the plant, particularly on aerial or aboveground parts of the plant, such as the leaves. As used herein, "inhibiting infection" refers to the production of a reduced fungal infection in the rice plant, as measured by a reduction in the symptoms of the fungal infection, for example, by a reduced number of lesions on the aerial portions of the rice plant compared to an untreated plant, or a reduced size of some or all of the lesions. For example, in particular embodiments, *Bacillus subtilis* FB17 is administered to a rice plant, the seed of the rice plant, or soil surrounding the rice plant or the seed in an amount effective to reduce the number of lesions on the rice plant caused by rice blast by about 5% to about 100%, about 10% to about 80%, about 20% to about 60%, or about 25% to about 45%, compared to an untreated rice plant. Without being bound to any theory, it is believed that *B. subtilis* FB17 produces an antifungal volatile compound which attenuates or inhibits *M. oryzae*'s growth. In particular embodiments, in order to inhibit the growth of rice blast and infection of a rice plant, *Bacillus subtilis* FB17 is administered to a rice seed in an amount of between about $1 \times 10^7$ CFU/seed to about $1 \times 10^9$ CFU/seed, more preferably about $1 \times 10^8$ CFU/seed, and the seed is subsequently planted in soil.

As used herein, an "untreated plant" refers to a plant of the same species and grown under substantially the same conditions (e.g., for the same amount of time, in the same climate, and cultivated according to the same methods using the same materials, with biomass, drought tolerance, lignin concentration, iron concentration, fungal infection, and other characteristics being measured according to the same methods) as a plant which has been administered *Bacillus subtilis* FB17 according to a method of the present invention, except that the untreated plant has not been administered *Bacillus subtilis* FB17. As used herein, a characteristic of a plant that has been administered *Bacillus subtilis* FB17, such as a greater biomass, greater drought tolerance, decreased lignin concentration, greater iron concentration, or decreased fungal infection, compared to an untreated plant, refers to a greater biomass, greater drought tolerance, decreased lignin concentration, greater iron concentration, or decreased fungal infection as measured at the same timepoint, respectively.

In certain embodiments of the methods described herein, *Bacillus subtilis* FB17 is administered to a seed in an amount of between about 1 ml/kg of a *Bacillus subtilis* FB17 inoculum (i.e., 1 ml/kg of 0.5 Optical Density (OD) at wavelength 600 nm as measured using a SmartSpec Bio Rad spectrophotometer of *Bacillus subtilis* FB17 grown overnight in LB medium) to about 50 ml/kg, preferably between about 5 ml/kg to about 25 ml/kg, more preferably between about 10 ml/kg to about 15 ml/kg, most preferably about 12.5 ml/kg. In alternative embodiments, the *Bacillus subtilis* FB17 is administered to a seed in an amount of between about $1 \times 10^6$ CFU/seed to about $1 \times 10^9$ CFU/seed, more preferably between about $1 \times 10^7$ CFU/seed to about $1 \times 10^8$ CFU/seed.

The methods of the present invention can be used to treat many types of plants (as well as their seeds or surrounding soil) to increase biomass, increase drought tolerance, decrease lignin content, increase seed germination, increase iron concentration, and increase tolerance to pathogens. The plants may include monocots or dicots. In particular, the plants may include crops such as corn, soybean, tomato, rice, or barley. Additional examples of plants that can be treated according to methods of the present invention include *Arabidopsis thaliana* and *Zinnia*, as well as bioenergy crop plants, i.e., plants that are currently used or have the potential to be used as sources of bioenergy (e.g., plants which are useful in producing biofuels), such as *Brachypodium distachyon*.

According to the invention, *Bacillus subtilis* FB17 may be administered to a plant by any known method wherein all or part of the plant is treated, such as by root, seed, or foliar inoculation. For example, *Bacillus subtilis* FB17 can be administered to the aerial portions of a plant, such as the leaves and stem, to the roots of the plant, to the seed of the plant prior to planting the seed in soil, or to the soil surrounding the plant or plant seed. Methods of administration include drenching, spraying, coating, injection, or other methods known to those of ordinary skill in the art. As used herein, administering *Bacillus subtilis* FB17 refers to either one-time administration, repeated administration (i.e., administering *Bacillus subtilis* FB17 more than one time), or continuous administration. The *Bacillus subtilis* FB17 can be administered at any point in the life cycle of the plant (e.g., before or after germination). For example, *Bacillus subtilis* FB17 can be administered to a plant's seed prior to planting the seed in soil and prior to germination. Alternatively, *Bacillus subtilis* FB17 can be administered to the plant, the seed of the plant, or the soil surrounding the plant after germination has occurred. Once treated with *Bacillus subtilis* FB17, seeds can be planted in soil and cultivated using conventional methods for generating plant growth.

According to embodiments of the present invention, *Bacillus subtilis* FB17 can be administered to a plant, plant seed, or soil either alone or in a mixture with other materials. For example, *Bacillus subtilis* FB17 can be administered in a composition that consists essentially of *Bacillus subtilis* FB17 in a growth medium without any additional additives or materials. Alternatively, *Bacillus subtilis* FB17 can be administered in a composition that comprises *Bacillus subtilis* FB17 in a growth medium, a carrier, such as water, an aqueous solution, or a powder. The growth medium, carrier, aqueous solution, or powder may contain additional additives, such as an insecticide or fungicide. Alternatively, *Bacillus subtilis* FB17 can be administered separately with other additives or materials being applied at different times. In certain embodiments, *Bacillus subtilis* FB17 is administered in a composition that comprises *Bacillus subtilis* FB17 in an amount of between about 1 ml/kg (i.e., 1 ml/kg of 0.5 Optical Density (OD) at wavelength 600 nm as measured using a SmartSpec Bio Rad spectrophotometer of *Bacillus subtilis* FB17 grown overnight in LB medium) to about 50 ml/kg, preferably between about 5 ml/kg to about 25 ml/kg, more preferably between about 10 ml/kg to about 15 ml/kg, most preferably about 12.5 ml/kg. In alternative embodiments, *Bacillus subtilis* FB17 is administered in a composition that comprises *Bacillus subtilis* FB17 in an amount of between about $1 \times 10^6$ CFU/seed to about $1 \times 10^9$ CFU/seed, more preferably between about $1 \times 10^7$ CFU/seed to about $1 \times 10^8$ CFU/seed.

The present invention further provides agricultural carriers comprising *Bacillus subtilis* FB17, which can be applied to plants (e.g., roots), to soil surrounding the plants, or to seeds prior to planting, as well as seed coatings comprising *Bacillus subtilis* FB17 which can be applied to plant seeds. The present invention also provides a plant seed, preferably a crop plant seed (e.g., the seed of a corn plant, a soybean plant, a rice plant, a tomato plant, or a bioenergy crop plant such as *Brachypodium distachyon*), that is coated with *Bacillus subtilis* FB17, such that all or part of the seed has a coating or film comprising *Bacillus subtilis* FB17. The agricultural carrier may comprise *Bacillus subtilis* FB17 in an amount of between about 1 ml/kg of a *Bacillus subtilis* FB17 inoculum (i.e., 1 ml/kg of 0.5 Optical Density (OD) at wavelength 600 nm as measured using a SmartSpec Bio Rad spectrophotometer of *Bacillus subtilis* FB17 grown overnight in LB medium) to about 50 ml/kg, between about 5 ml/kg to about 25 ml/kg, between about 10 ml/kg to about 15 ml/kg, or about 12.5 ml/kg. The seed coating may comprise *Bacillus subtilis* FB17 in an amount of between about $1 \times 10^6$ CFU/seed to about $1 \times 10^8$ CFU/seed, more preferably about $1 \times 10^7$ CFU/seed. The agricultural carrier and seed coating may each consist essentially of *Bacillus subtilis* FB17 in a growth medium without any additional additives or materials. Alternatively, the agricultural carrier and seed coating may each comprise *Bacillus subtilis* FB17 in a growth medium, such as water, an aqueous solution, or a powder. The growth medium, aqueous solution, or powder may contain additional additives, such as an insecticide or fungicide.

The present invention has both basic and applied applications. In a broad sense one could use the methods described herein to increase biomass (e.g., in alternative plant species used for biofuel or to impact yield potential of crop plants) and to confer enhanced drought tolerance. Compared to transgenic approaches, these methods are immediately applicable to any plant, without the time required for gene identification, generation and characterization of transgenic lines, and is free of the regulatory and social issues related to the use of trans genes. Compared to the use of traditional agronomic practices (applications of chemical fertilizers and water), the methods described herein are less resource and labor intensive for the grower and are more environmentally friendly. In addition, application of chemical fertilizers is known to enhance crop disease susceptibility by the induction of rapid weak growth, whereas plants grown with this method do not demonstrate enhanced disease susceptibility. Compared to other rhizobacteria that are used for seed treatment, FB17 requires low inoculums to confer beneficial results. Finally, these methods are compatible with organic farming practices, whereas other methods described above (e.g., the application of chemical fertilizers) are not.

A deposit of *B. subtilis* strain FB17 has been available since prior to Mar. 1, 2010, at the Delaware Biotechnology Institute, 15 Innovation way, Room #145, Newark, Del. 19711. A deposit of *B. subtilis* strain FB17 was also made with the American Type Culture Collection (ATCC), 10801 University Boulevard, Manassas, Va. 20110-2209 USA on Apr. 26, 2011, under Accession No. PTA-11857. Access to this ATCC deposit will be available during the pendency of the application to the Commissioner of Patents and Trademarks and persons determined by the Commissioner to be entitled thereto upon request. The deposit will be maintained in the ATCC Depository, which is a public depository, for a period of 30 years, or 5 years after the most recent request, or for the enforceable life of the patent, whichever is longer, and will be replaced if it becomes nonviable during that period. The deposit will be available as required by foreign patent laws in countries wherein counterparts of the subject application, or its progeny are filed.

Further, the subject deposit will be stored and made available to the public in accord with the provisions of the Budapest Treaty for the Deposit of Microorganisms, i.e., it will be stored with all the care necessary to keep it viable and uncontaminated for a period of at least five years after the most recent request for the furnishing of a sample of the deposit, and in any case, for a period of at least thirty (30) years after the date of deposit or for the enforceable life of any patent which may issue disclosing the culture.

The following examples are provided to describe the invention in greater detail and are intended to illustrate, not limit, the invention. "UD10-22," as stated in some of the figures described below, refers to *Bacillus subtilis* FB17.

EXAMPLES

Example 1

*Brachypodium distachyon* and corn plants were germinated and grown for 21 days. Once in 5 days (3 times), 5 ml of 0.5 OD *B. subtilis* FB17 per pot was added. For control, 5 ml of 0.5 OD of *E. coli* OP50 per pot was added. FB17 and OP50 had been grown overnight in LB medium and optical density (OD) at wavelength (600 nm) was taken using SmartSpec (Bio Rad) spectrophotometer. Ten days after the final treatment, plants were analyzed. The controls described in all the experiments herein refer to plants that were not treated with bacteria or that were treated with *E. coli* OP50.

Figure 1:
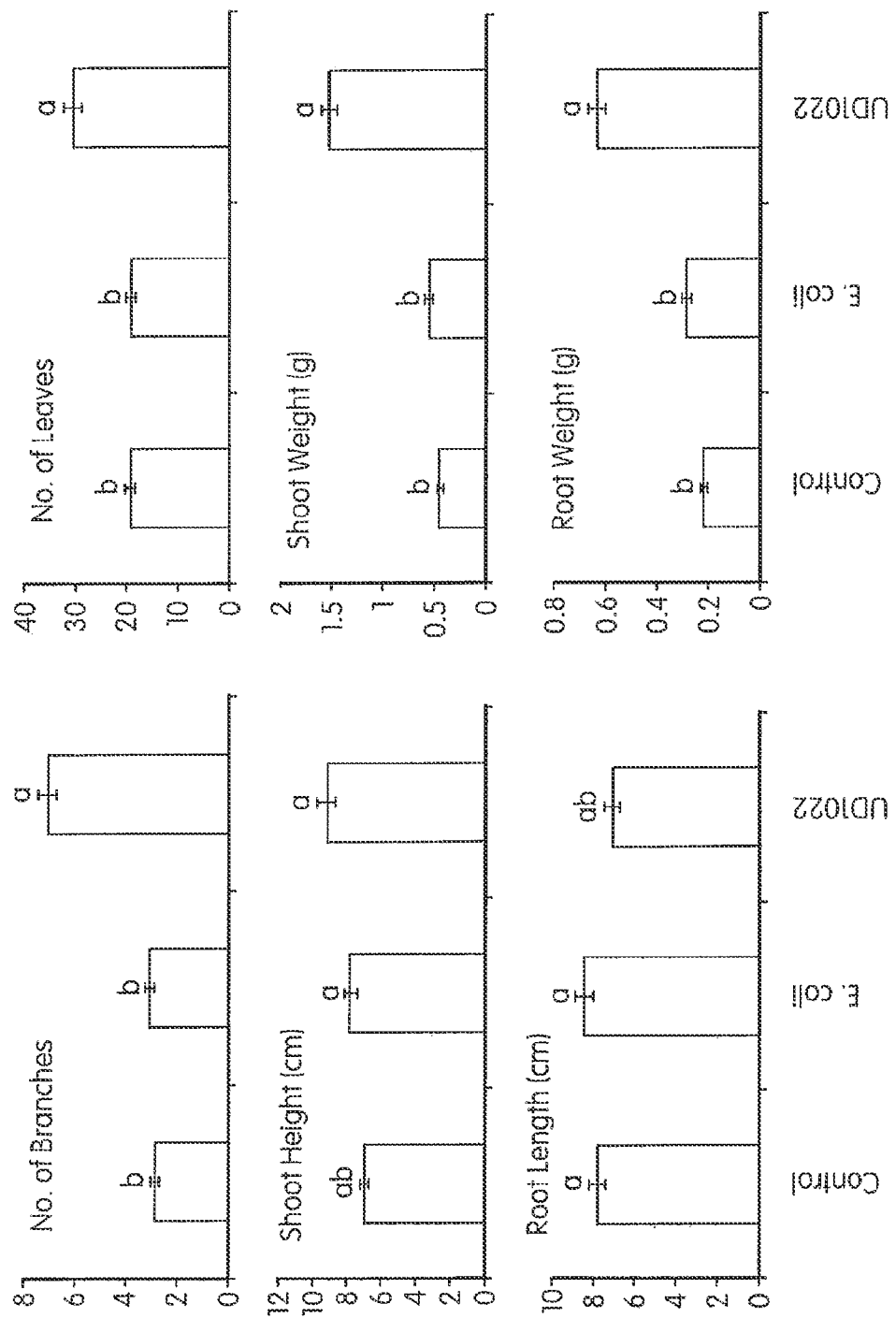
FIG. 1: Morphometric analysis (number of branches, number of leaves, shoot height, shoot weight, root length, root weight) of *Brachypodium distachyon* (Bd2-1) plants treated with *B. subtilis* FB17 compared to controls. This shows that inoculation with *B. subtilis* FB17 enhances plant morphology.
Figure 2:
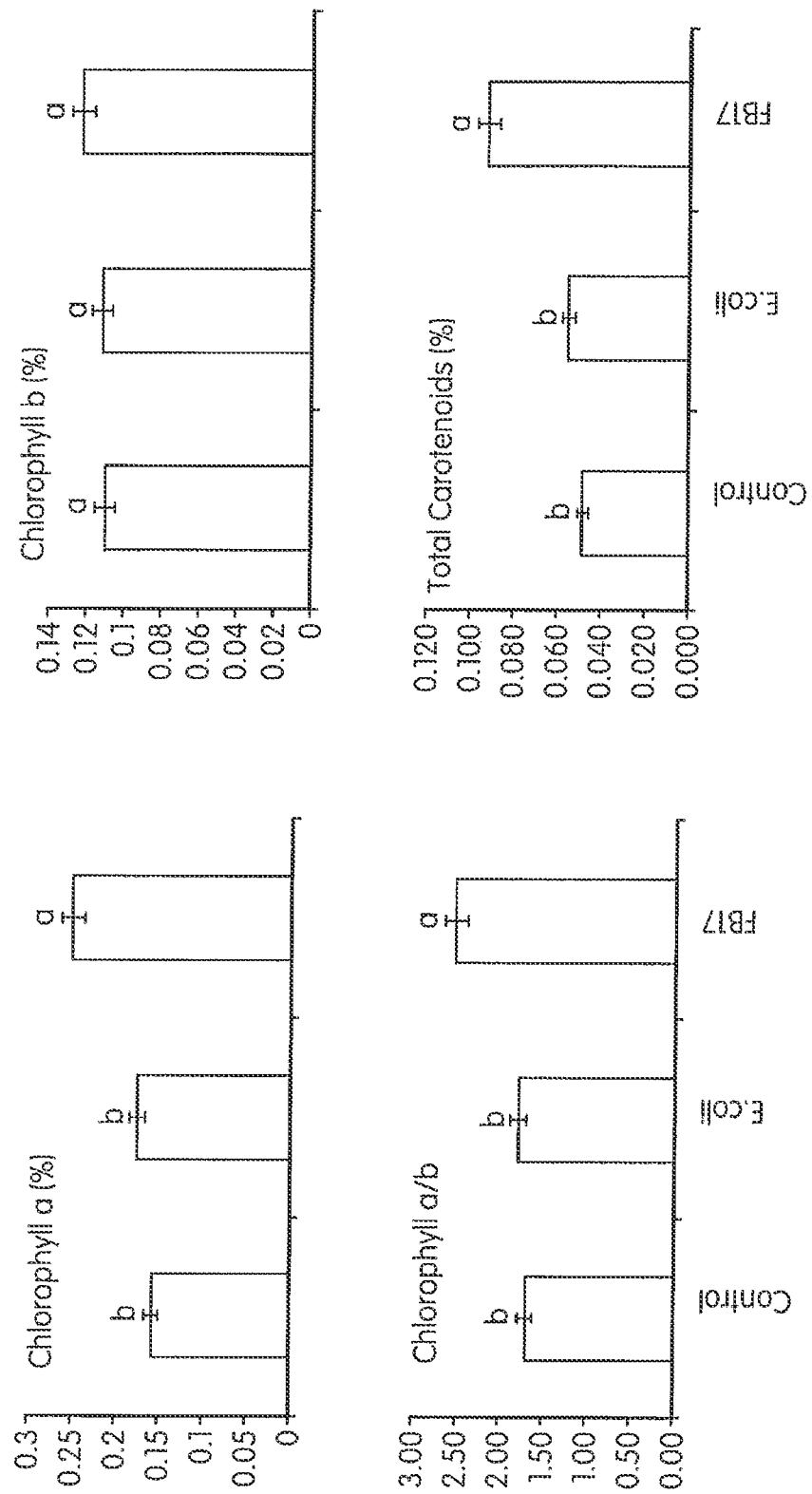
FIG. 2: Biochemical analysis of *Brachypodium distachyon* plants treated with *B. subtilis* FB17 compared to controls, as measured by total chlorophyll and carotenoids. This shows that *B. subtilis* FB17 inoculation positively impacts the ability of plants to collect light energy.
Figure 3:
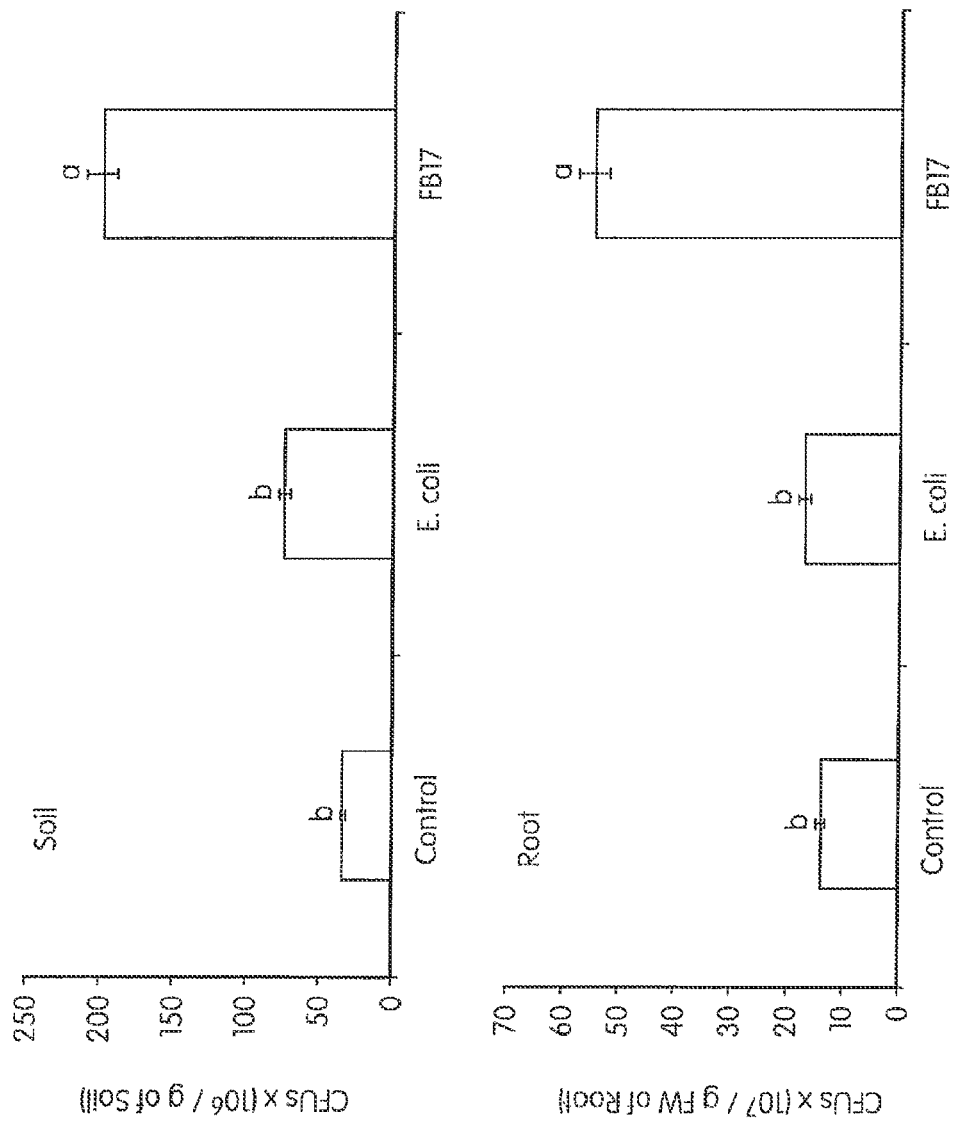
FIG. 3: Amounts of *B. subtilis* FB17 and controls recovered from soil and *Brachypodium distachyon* roots. This demonstrates persistence of association with the root of *B. subtilis* FB17 inoculated plants.

*Brachypodium distachyon* (Bd2-1) and corn plants treated with *B. subtilis* FB17, bacterial control *E. coli*, or mock treatment were grown in 4×4 inch pots in standard conditions (22-25° C., 60% humidity, 16 h light-8 h dark photoperiod) for 30 days post treatment. Aerial and root biomass of the energy crop *B. distachyon* increased with FB17 treatment. FIG. 1 shows that the biomass of *B. distachyon* treated with FB17 was enhanced at a statistical level. FIG. 2 depicts an increase in photosynthetic efficiency observed in *B. distachyon* treated with FB17. The *B. distachyon* treated with FB17 contained more chlorophyll and total caroetenoids than controls, demonstrating robust plant health. FIG. 3 shows amounts of FB17 recovered from soil surrounding *B. distachyon* roots. The figure reveals that FB17 is associated much more strongly with *B. distachyon* roots compared to the *E. coli*, suggesting the true rhizobacterial nature of FB17.

Corn plants also exhibited an increase in aerial and root biomass after growing for 30 days following treatment with *B. subtilis* FB17, bacterial control *E. coli* OP50, or mock treatment.

Example 2

*Arabidopsis thaliana* seeds were germinated and grown for 21 days. Once in 5 days (3 times), 5 ml of 0.5OD *B. subtilis* FB17 per pot was added. For control, 5 ml of 0.50D of *E. coli* OP50 per pot was added. FB17 and OP50 had been grown overnight in LB medium and optical density (OD) at wavelength (600 nm) was taken using SmartSpec (Bio Rad) spectrophotometer. Ten days after the final treatment, plants were subjected to drought (i.e., no water was added) at 25° C. with 40% humidity for 4 weeks. Thirty days post-treatment, drought was assessed through loss of stay green phenotype in the untreated plants compared to the FB17 treated plants, indicating that FB17 confers enhanced drought tolerance in *Arabidopsis*.

Example 3

Seed treatment of *B. subtilis* FB17 promotes biomass enhancement in Corn Mo17, CML258, CML10, *Zinnia*, and *Brachypodium distachyon*.

To test the effect of *B. subtilis* FB17 on biomass enhancement in corn (Mo17, CML258, CML10), soybean (Will-82), tomato (*Solanum lycopersicum*), *Zinnia*, and *Brachypodium distachyon* (an energy crop model), 50 seeds (n=50) per plant species were seed treated with *B. subtilis* FB17 (about $1\times10^7$ cfu/seed or 12.5 ml/kg of 0.5 Optical Density (OD) *Bacillus subtilis* FB17 grown overnight in LB medium, at wavelength 600 nm as measured using a SmartSpec Bio Rad spectrophotometer). Post seed treatment seeds were individually sown in pots (4×4 inches) with a soil mix for germination and biomass studies. Interestingly, seed treatment of *B. subtilis* FB17 promoted root and shoot growth for all the tested crop species. Measurements were taken 15 days post treatment.

Seed treated plants promoted increased root biomass resulting in denser root systems rather than increased root length. A denser root system results from increased lateral roots and root hairs providing more available uptake of water and nutrients.

*Zea mays* var. CML258 resulted in about 16% increase in aerial biomass (g DW) over control. *Zea mays* var. CML10 resulted in about 9% increase in aerial biomass (g DW) over control. *Zea mays* var. Mo-17 resulted in about 38% increase in aerial biomass (g DW) over control. *Brachypodium* resulted in about 40% increase in aerial biomass (g DW) over control. A significant increase of about 28% in total aerial and root biomass was observed with *Z. mays* (MO17) over control. FIG. 4 illustrates the total biomass gain in plants treated with *B. subtilis* FB17.

Figure 5:
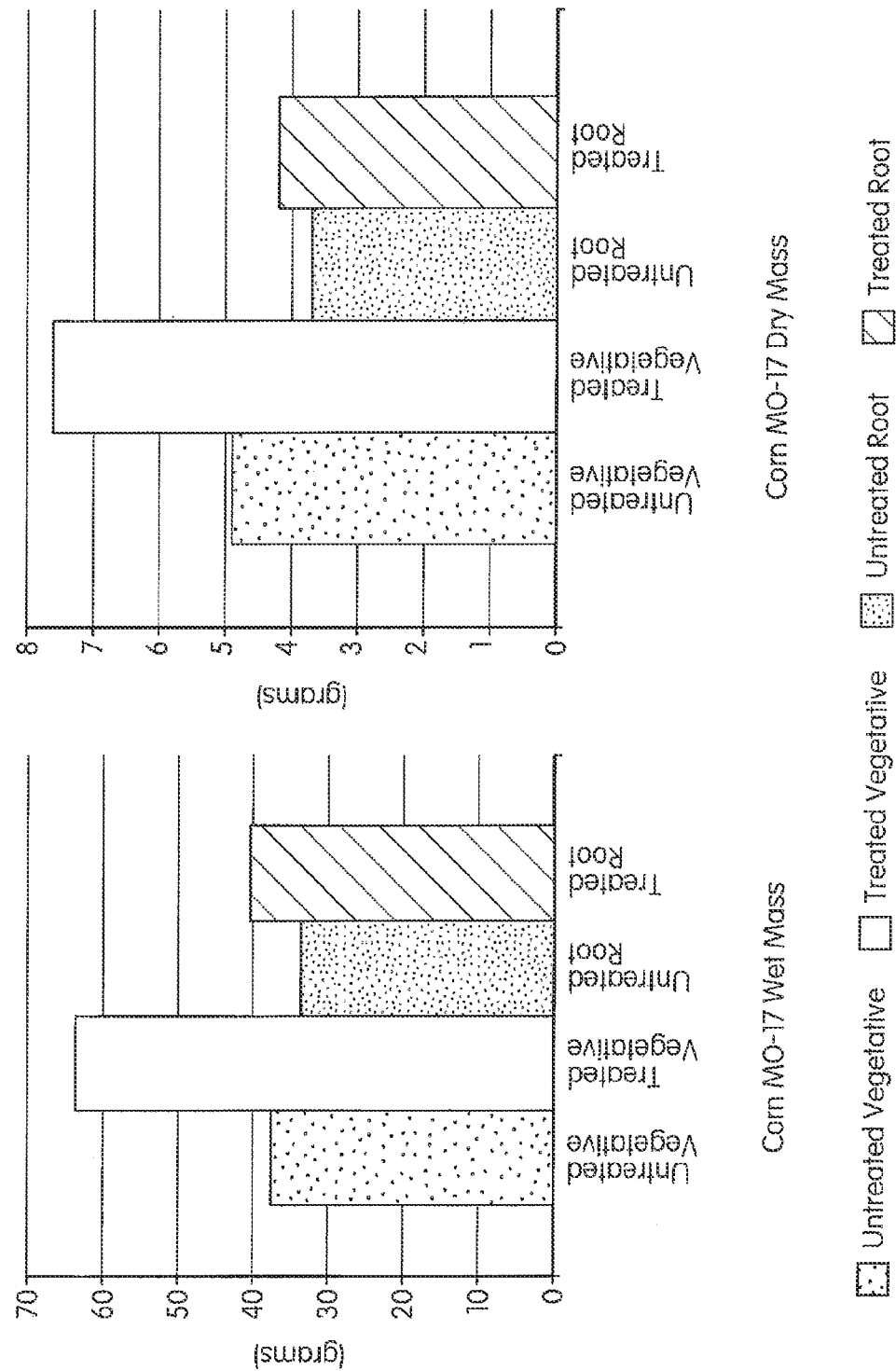
FIG. 5: Quantitative data showing the increased root and shoot biomass in the *B. subtilis* FB17 seed treated *Z. mays* Mo-17 plants.
Figure 6:
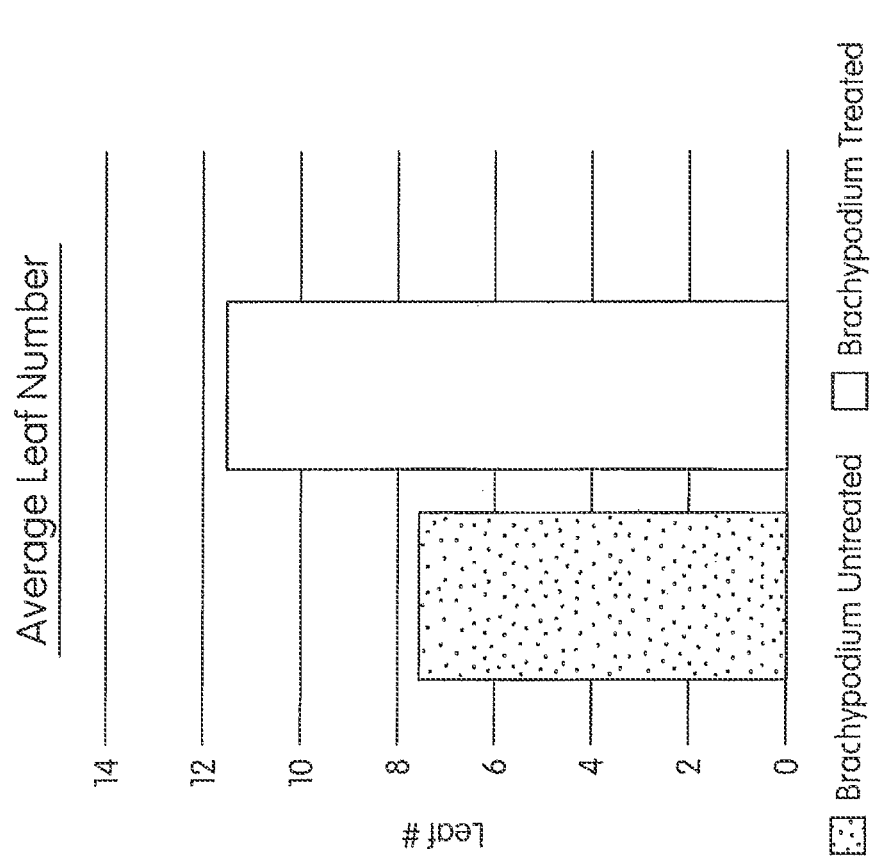
FIG. 6: Quantitative data showing the increased leaf numbers in the *B. subtilis* FB17 seed treated bioenergy crop *Brachypodium distachyon* (genotype Bd2-1) plants.
Figure 7:
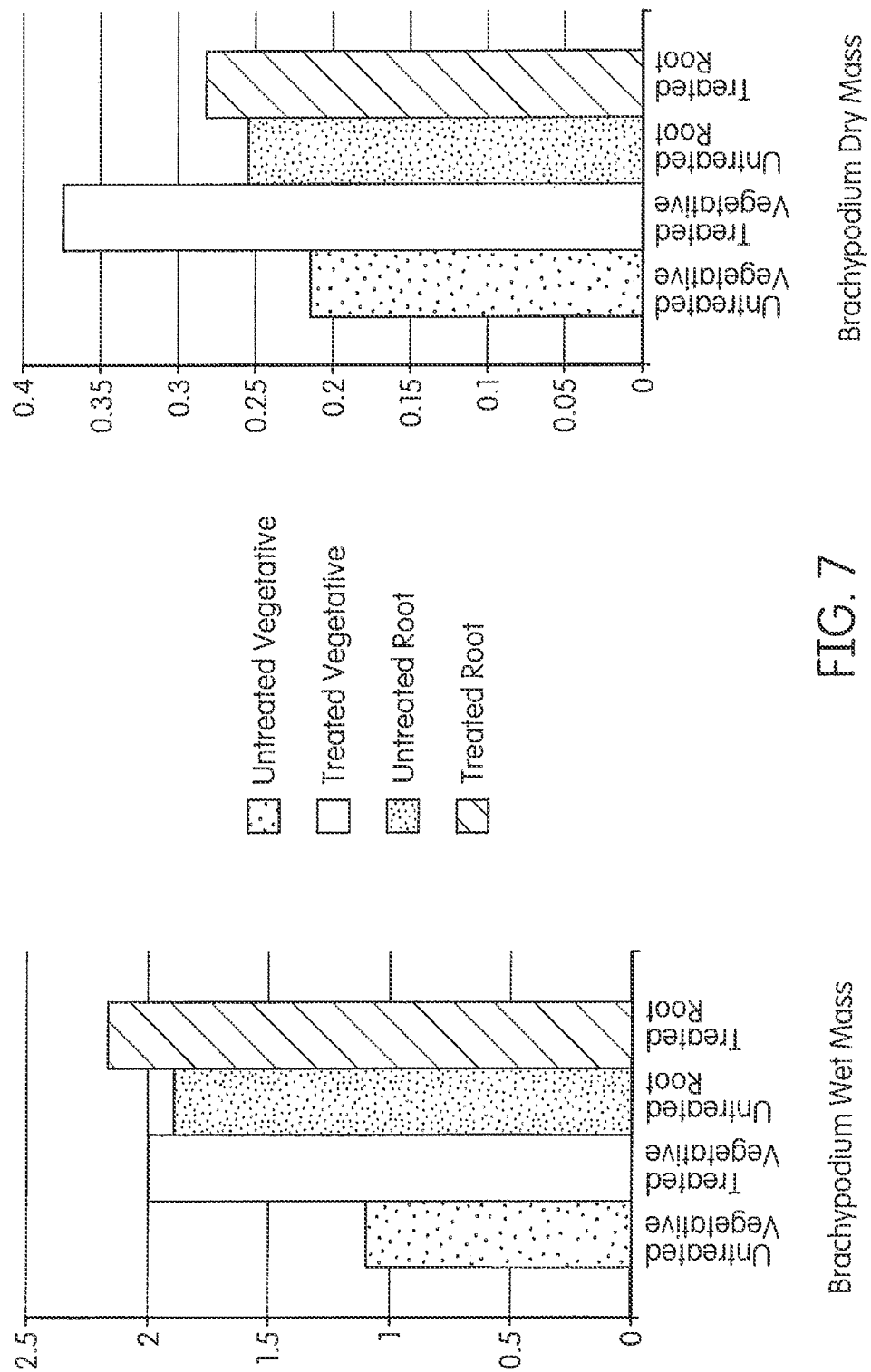
FIG. 7: Quantitative data showing the increased root and shoot biomass in the *B. subtilis* FB17 seed treated bioenergy crop *Brachypodium distachyon* (genotype Bd2-1) plants.
Figure 8:
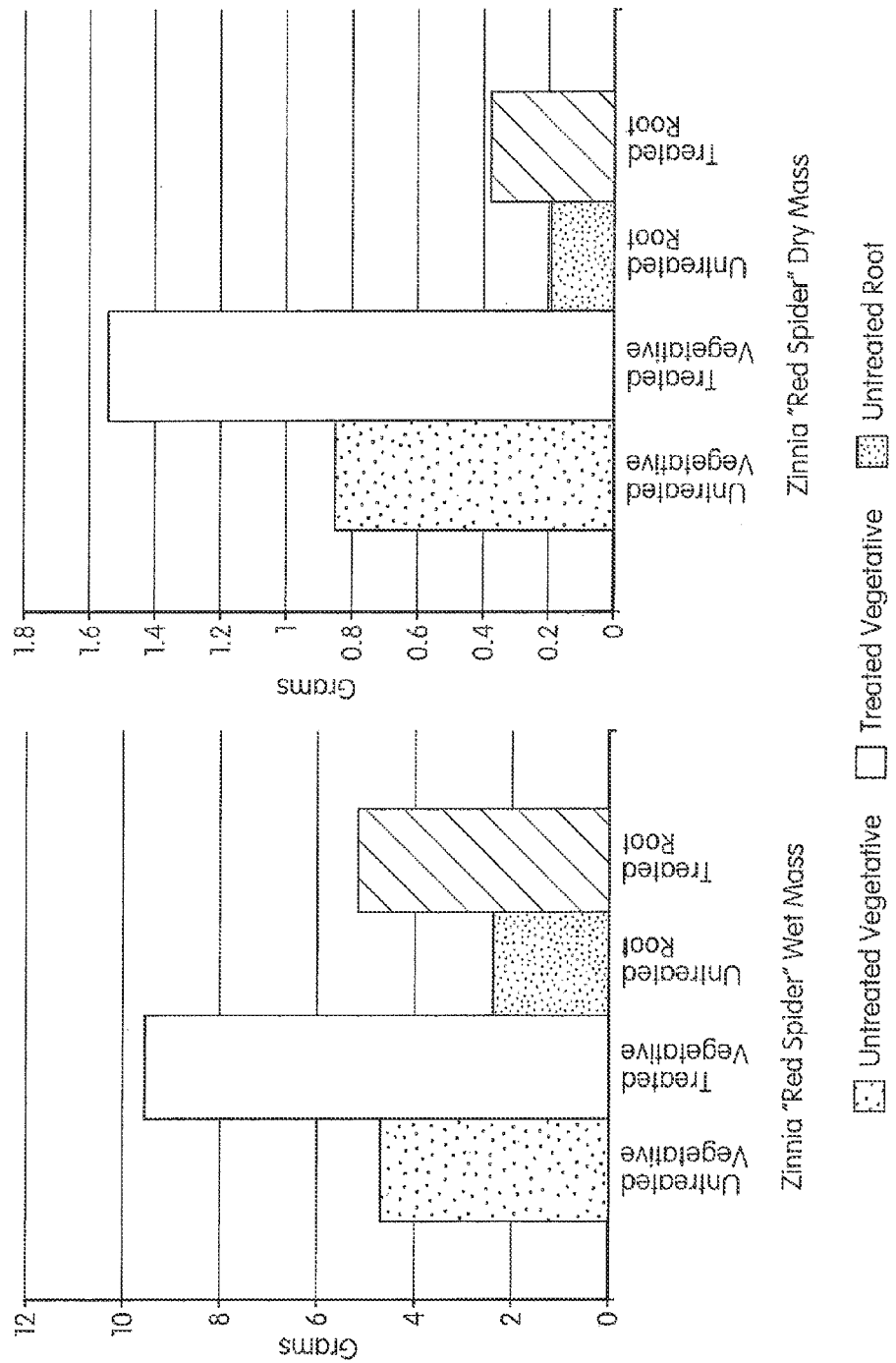
FIG. 8: Quantitative data showing the increased root and shoot biomass in the *B. subtilis* FB17 seed treated *Zinnia* sp. 'Red Spider'.
Figure 9:
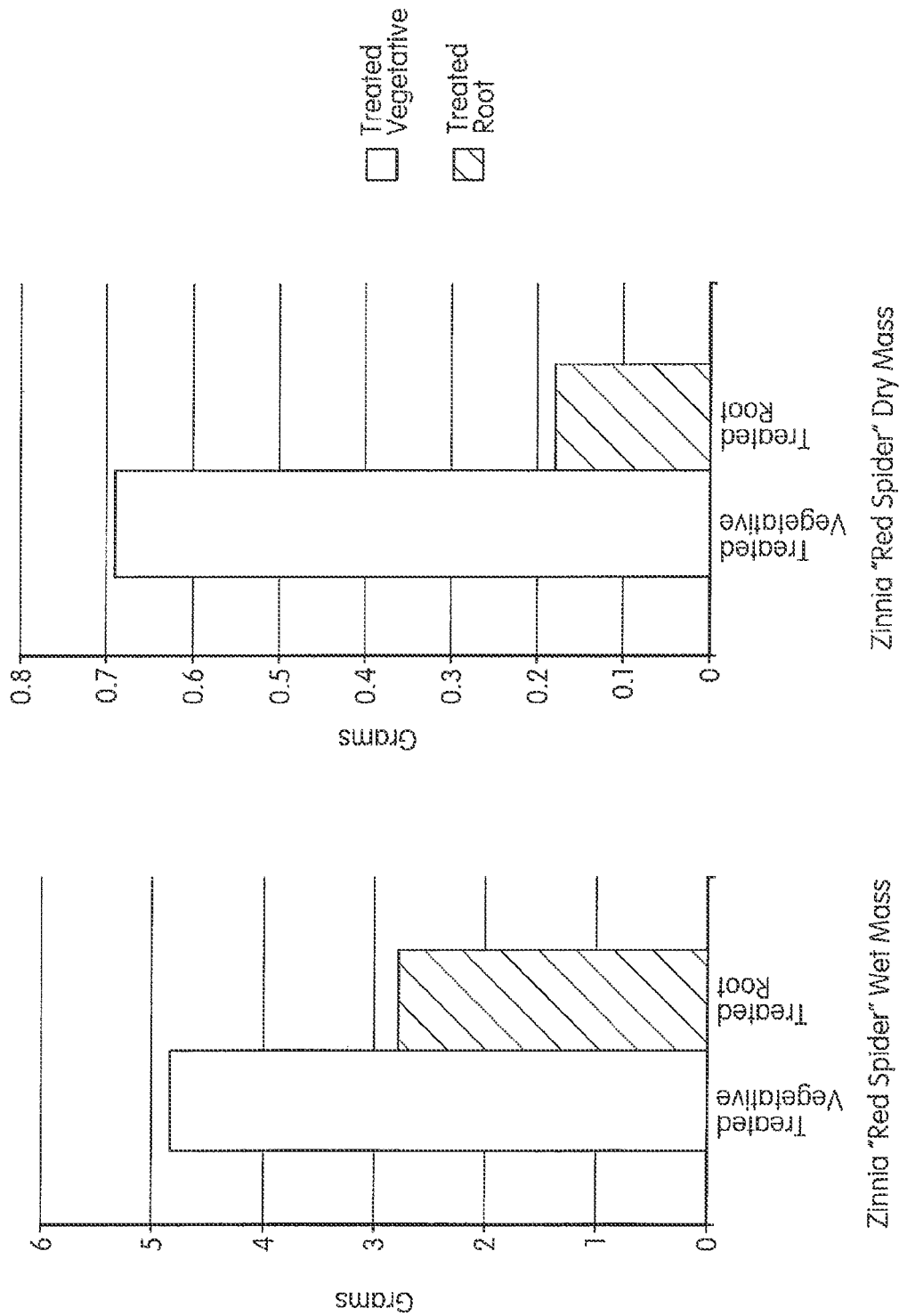
FIG. 9: Quantitative data showing the increased root and shoot biomass in the *B. subtilis* FB17 seed treated *Zinnia* sp. 'Red Spider'.

FIG. 5 illustrates quantitative data showing the increased root and shoot biomass in the *B. subtilis* FB17 seed treated Mo-17 plants. FIG. 6 illustrates quantitative data showing the increased leaf numbers in the *B. subtilis* FB17 seed treated bioenergy crop *Brachypodium distachyon* (genotype Bd2-1) plants. FIG. 7 illustrates quantitative data showing the increased root and shoot biomass in the *B. subtilis* FB17 seed treated bioenergy crop *Brachypodium distachyon* (genotype Bd2-1) plants. FIGS. 8 and 9 illustrate quantitative data showing the increased root and shoot biomass in the *B. subtilis* FB17 seed treated *Zinnia* sp. 'Red Spider'.

Example 4

Seed treatment of *B. subtilis* FB17 promotes photosynthetic efficiency in corn and tomato.

Figure 10:
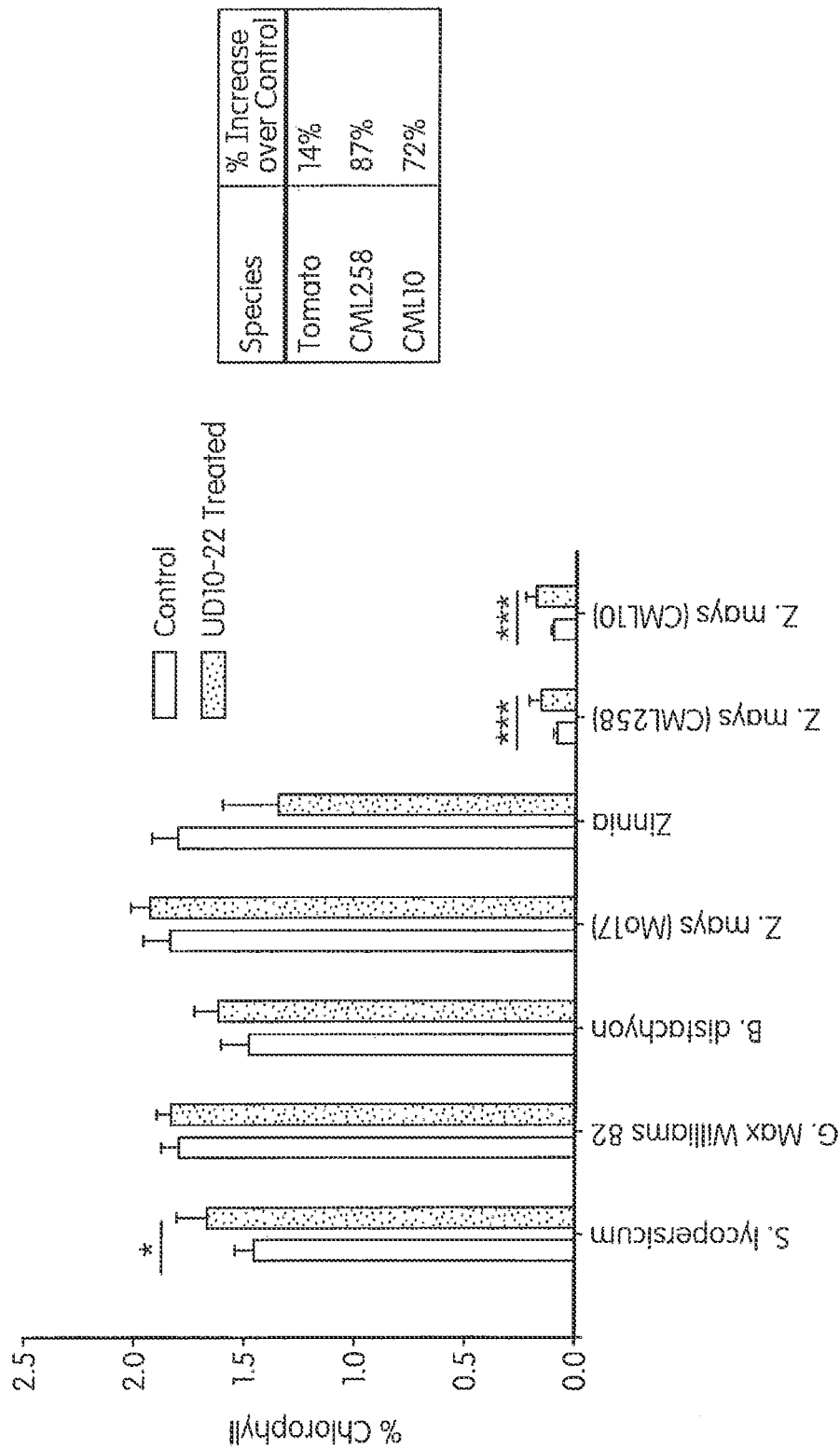
FIG. 10: Total chlorophyll content in plants treated with *B. subtilis* FB17. Significant increase in total chlorophyll content was observed in tomato (14%), *Z. mays* CML10 (72%) and CML258 (87%) post FB17 treatment.
Figure 11:
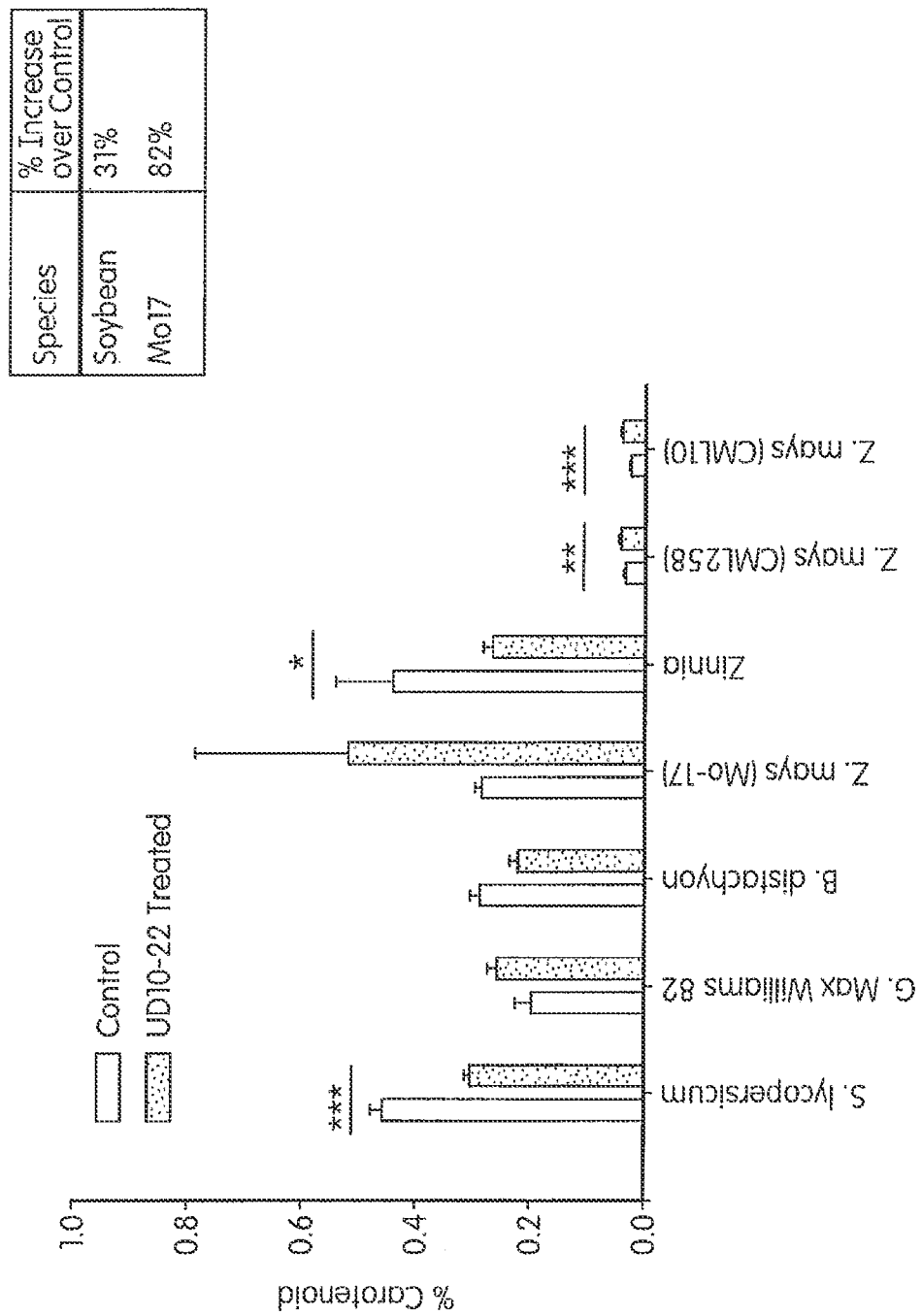
FIG. 11: Total carotenoid content in plants treated with *B. subtilis* FB17. Significant increase in total carotenoid content was observed in soybean (31%) and *Z. mays* MO17 (82%) post FB17 treatment.

To test the effect of *B. subtilis* FB17 on photosynthetic efficiency in corn (Mo17, CML258, CML10), soybean (Will-82), tomato (*Solanum lycopersicum*), *Zinnia*, and *Brachypodium* (an energy crop model), 50 seeds (n=50) per plant species were seed treated with *B. subtilis* FB17 (12.5 ml/kg or 1e7 cfu/seed). Leaves post 15-32 days of treatment were harvested and analyzed for total chlorophyll content. Results showed that *B. subtilis* FB17 inoculated corn and tomato plants (tomato and exotic lines of Corn CML258 and CML10) showed enhanced chlorophyll and carotenoid content compared to the untreated samples, as depicted in FIGS. 10 and 11.

The increased total chlorophyll values have the potential to promote increased vigor and biomass as seen with CML258 and CML10. The total chlorophyll content of *B. subtilis* FB17 seed inoculated tomatoes resulted in an increase of about 14%. Even more significant are exotic corn lines CML258 and CML10 with an increase of about 87% and about 72% increases, respectively.

Although there are increases in total chlorophyll content, that does not signify that the total carotenoid content will also correspond with an increased value. Tomato and *Zinnia* had significantly reduced total carotenoid percent when inoculated with *B. subtilis* FB17 and compared with untreated seeds. Corn CML258 and CML10 had significantly increased total carotenoid percents, while soybean, corn Mo17, and *Brachypodium* did not show statistically significant differences between treated and untreated seeds.

Figure 12:
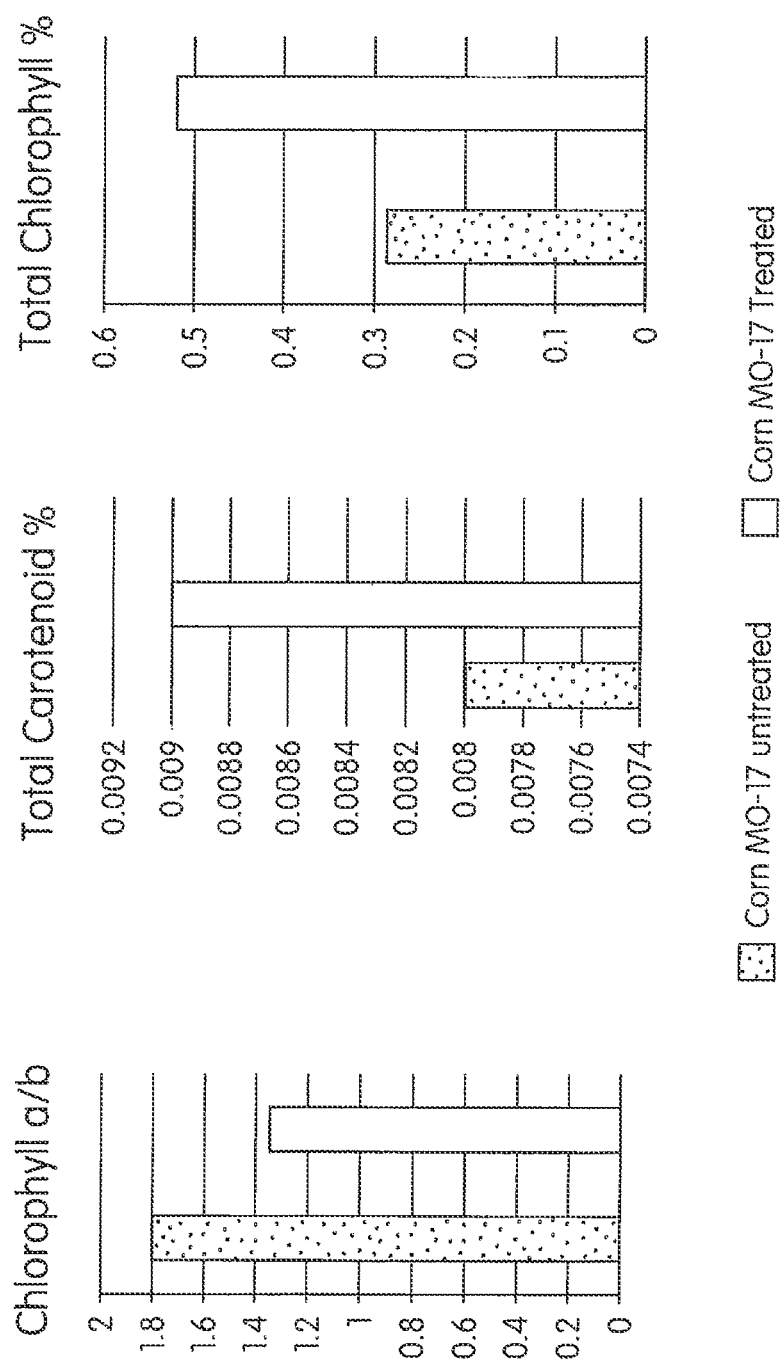
FIG. 12: Quantitative data showing the increased photosynthetic efficiency in the *B. subtilis* FB17 seed treated Mo-17 plants.
Figure 13:
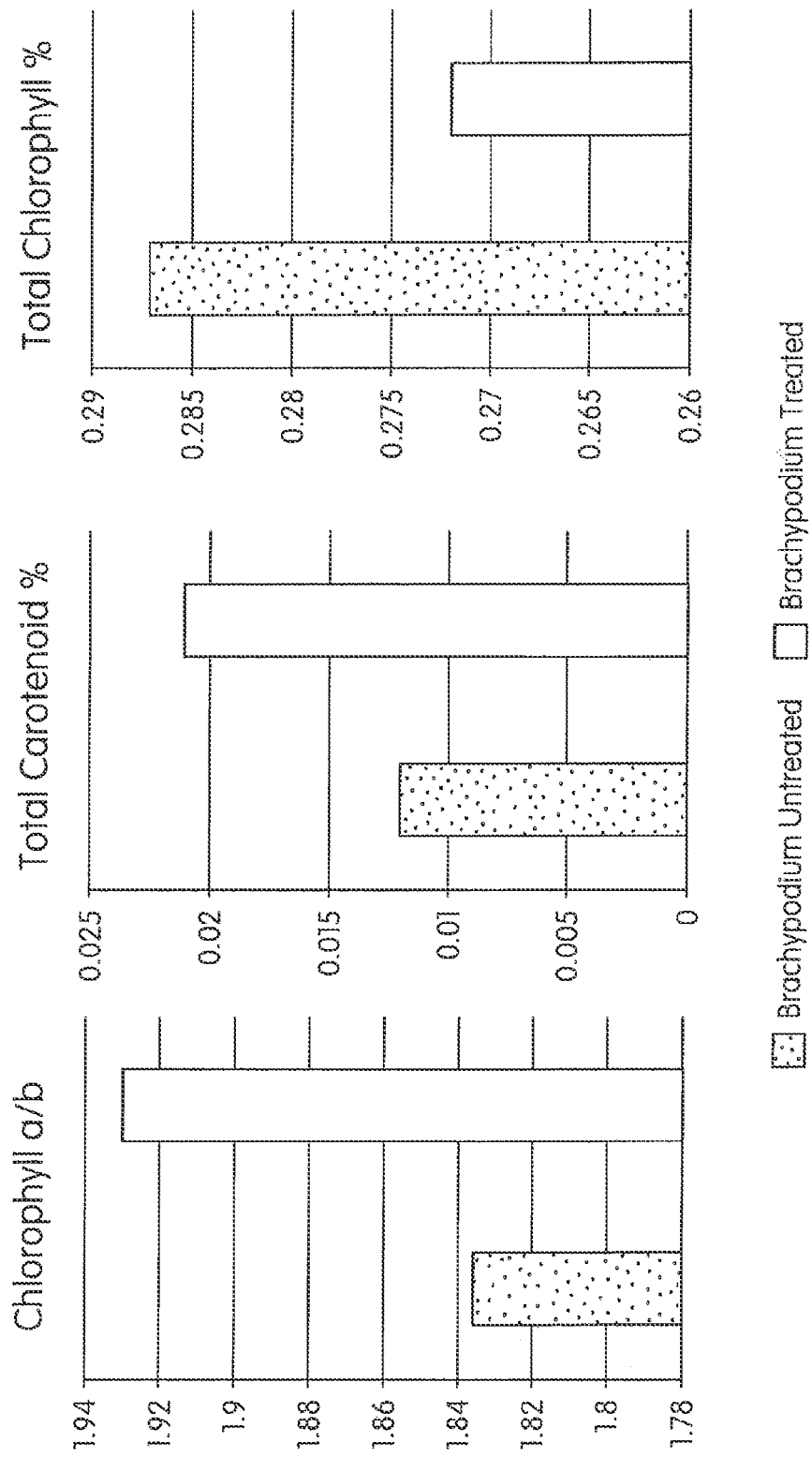
FIG. 13: Quantitative data showing the increased photosynthetic efficiency in the *B. subtilis* FB17 seed treated bioenergy crop *Brachypodium distachyon* (genotype Bd2-1) plants.
Figure 14:
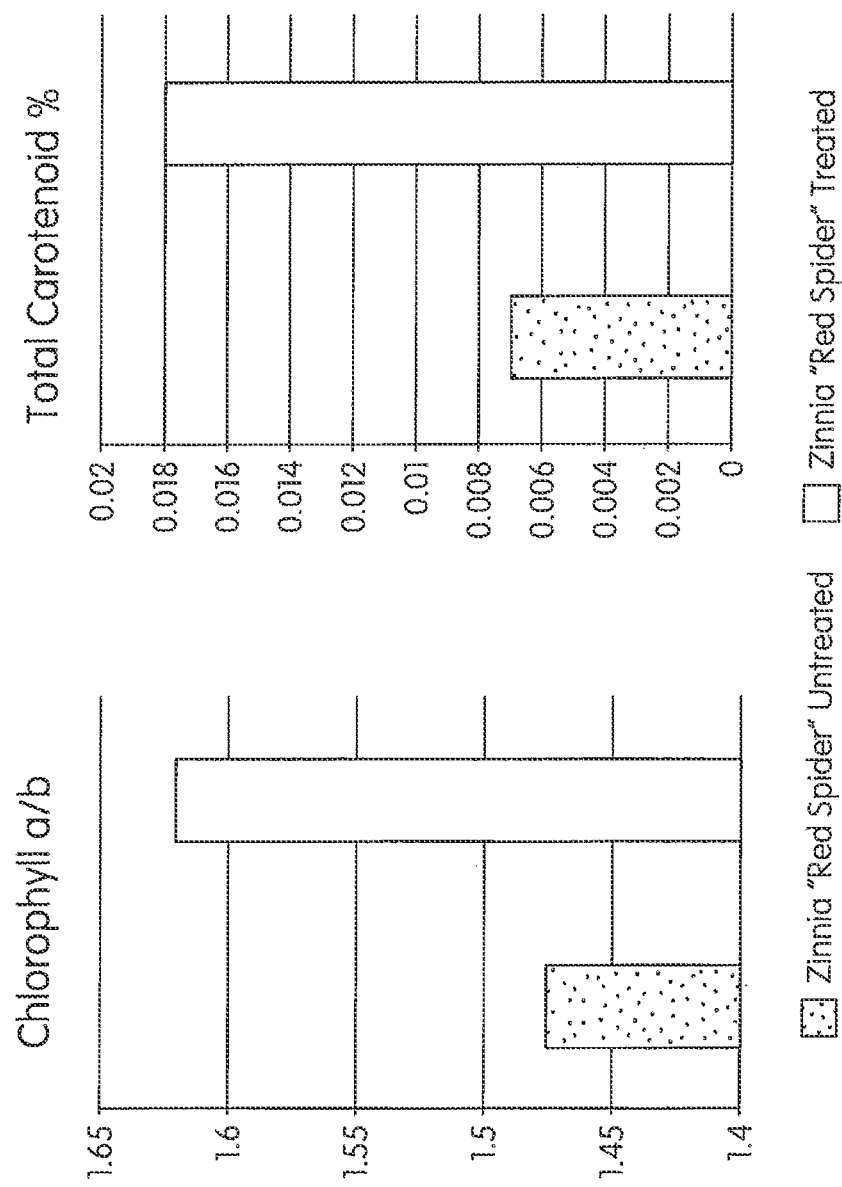
FIG. 14: Quantitative data showing the increased photosynthetic efficiency in the *B. subtilis* FB17 seed treated *Zinnia* sp. 'Red Spider'.
Figure 15:
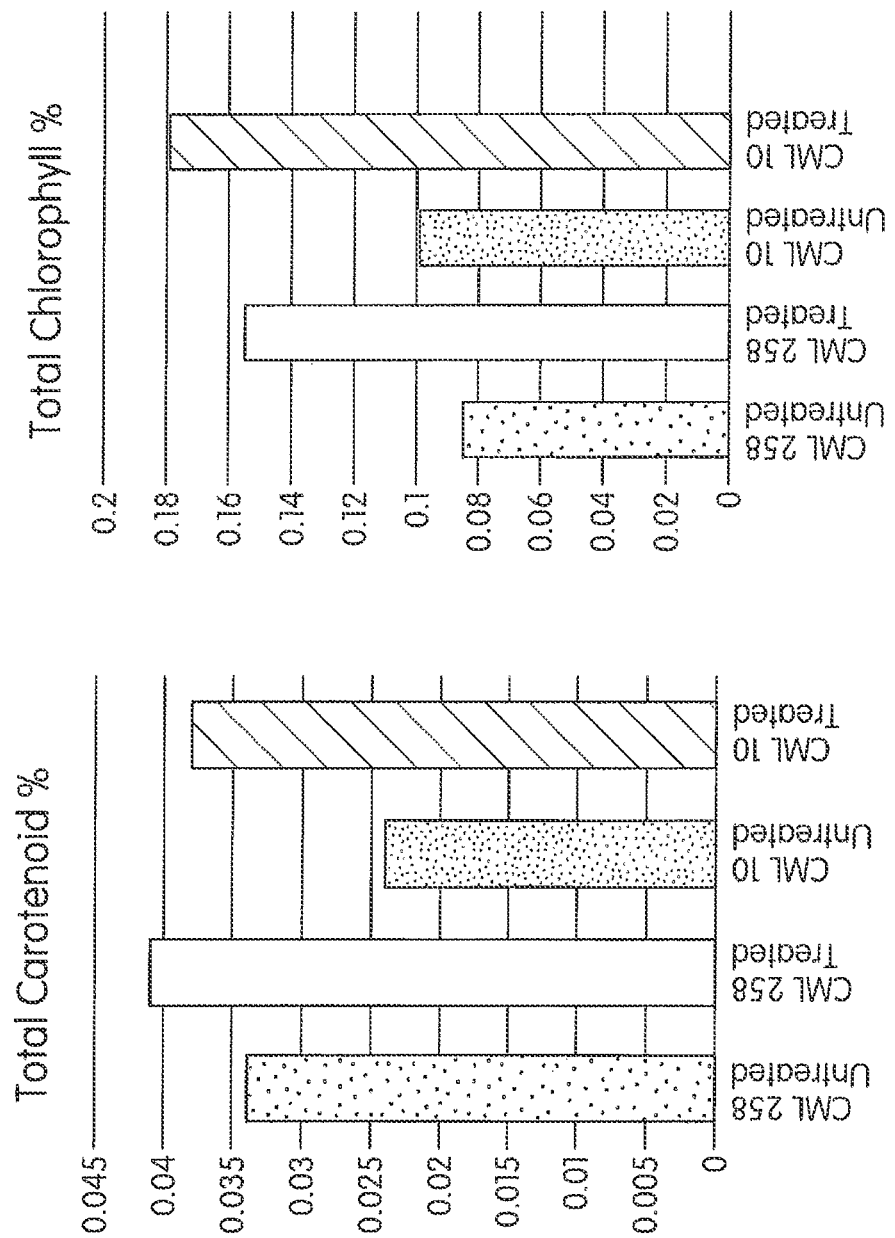
FIG. 15: Quantitative data showing the increased photosynthetic efficiency in the *B. subtilis* FB17 seed treated Exotic Corn CML 10 and CML 258.

FIG. 12 illustrates quantitative data showing the increased photosynthetic efficiency in the *B. subtilis* FB17 seed treated Mo-17 plants. FIG. 13 illustrates quantitative data showing the increased photosynthetic efficiency in the *B. subtilis* FB17 seed treated bioenergy crop *Brachypodium distachyon* (genotype Bd2-1) plants. FIG. 14 illustrates quantitative data showing the increased photosynthetic efficiency in the *B. subtilis* FB17 seed treated *Zinnia* sp. 'Red Spider'. FIG. 15 illustrates quantitative data showing the increased photosynthetic efficiency in the *B. subtilis* FB17 seed treated Exotic Corn CML 10 and CML 258.

Example 5

Seed treatment of *B. subtilis* FB17 promotes germination in corn and tomato plants.

To test the effect of *B. subtilis* FB17 on percentage germination increase in corn (Mo17, CML258, CML10), soybean (Will-82), tomato (*Solanum lycopersicum*), *Zinnia*, and *Brachypodium* (an energy crop model), 50 seeds (n=50) per plant species were seed treated with *B. subtilis* FB17 (12.5 ml/kg or 1e7 cfu/seed). Final germination percents were scored 8 days post date sown. Results showed that *B. subtilis* FB17 treatment promoted statistically significant germination response in tomato and corn, as depicted in FIG. 16.

*B. subtilis* FB17 treated tomato seeds and exotic corn line CML 258 had a 5.9% and 14% increase in germination percent, respectively.

The *B. subtilis* FB17 seed treatment had neutral and positive effects for all of the crop species tested. There was not a statistically negative response to germination percent when seed treatments were applied.

Example 6

To test the effect of *B. subtilis* FB17 in corn (Mo17, CML258, CML10), soybean (Will-82), tomato (*Solanum*

Figure 17:
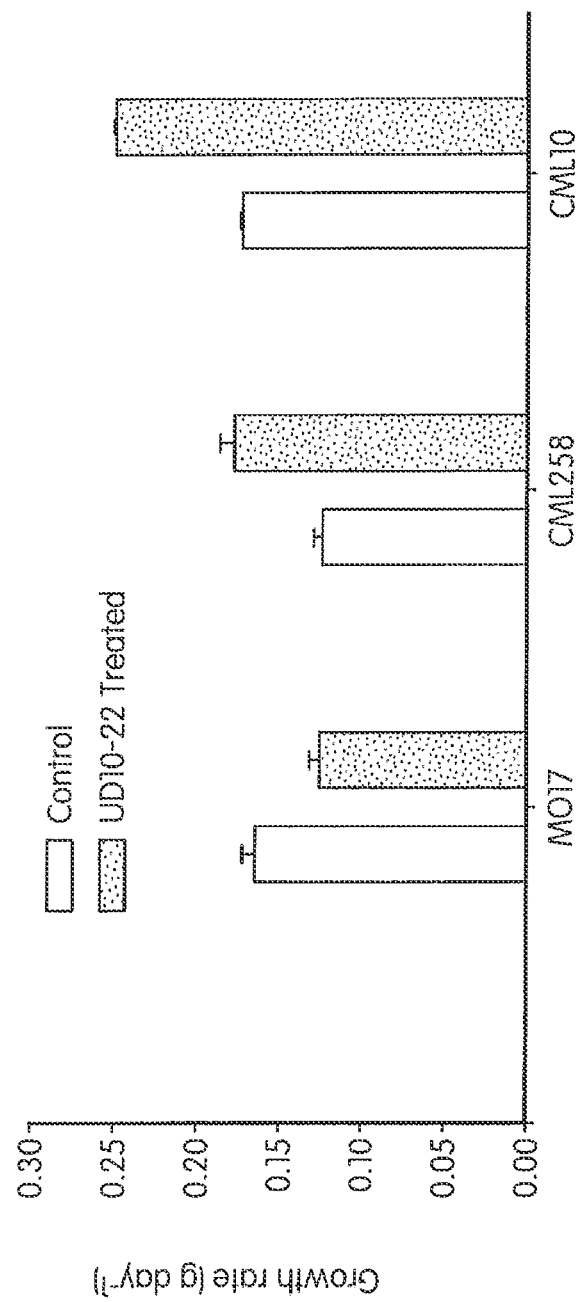
FIG. 17: Growth Rate in *Zea mays* treated with *B. subtilis* FB17.
Figure 18:
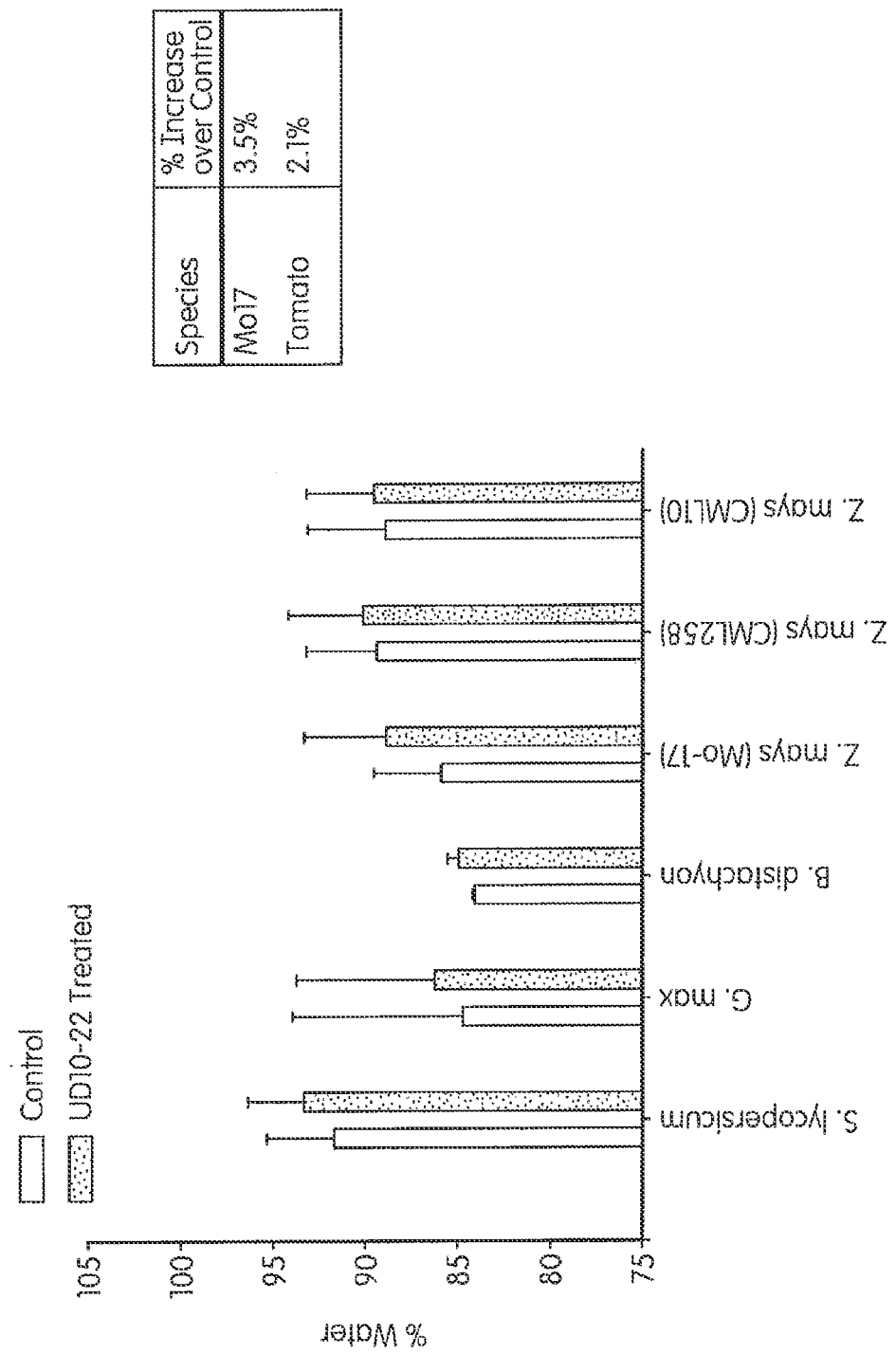
FIG. 18: Water holding capacity in plants treated with *B. subtilis* FB17. Significant increase in total water holding capacity and retention was observed in tomato (2.1%) and *Z. mays* MO17 (3.5%) post FB17 treatment.

*lycopersicum*), *Zinnia*, and *Brachypodium* (an energy crop model), 50 seeds (n=50) per plant species were seed treated with *B. subtilis* FB17 (1e7 cfu/seed or 12.5 ml/kg of 0.5 Optical Density (OD) *Bacillus subtilis* FB17 grown overnight in LB medium, at wavelength 600 nm as measured using a SmartSpec Bio Rad spectrophotometer). Post seed treatment seeds were individually sown in pots (4×4 inches). Measurements were made post 15 days of treatment. FIG. 17 illustrates the growth rate in *Zea mays* following treatment with *B. subtilis* FB17. FIG. 18 illustrates water holding capacity in plants treated with *B. subtilis* FB17. Significant increase in total water holding capacity and retention was observed in tomato (2.1%) and *Z. mays* MO17 (3.5%) post FB17 treatment. FIG. 19 illustrates drought tolerance in plants treated with *B. subtilis* FB17. Significant increase in growth rate under drought treatments was observed in MO17 (37.5% increase over no water treatment control) post FB17 treatment. FIG. 20 illustrates that *B. subtilis* FB17 seed treatment reduces lignin content in corn. Significant reduction of total lignin content was observed in *Z. mays* (about 46% reduction in MO17; about 64% reduction in CML10, and about 49% reduction in CML58) post FB17 treatment.

Example 7

Figure 21:
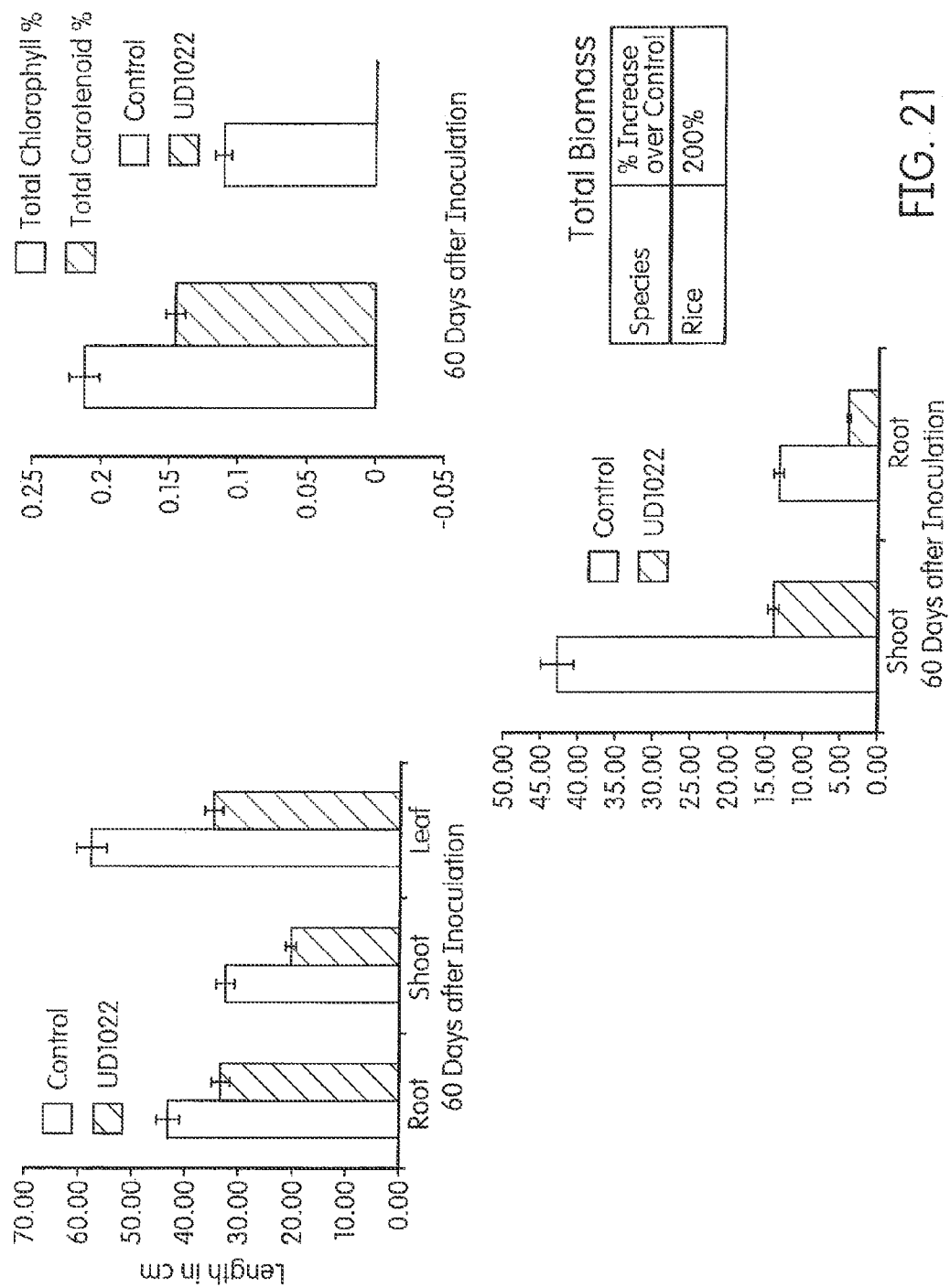
FIG. 21: Aerial & root biomass increase in *Oryza sativa* (Nipponbare) treated with *B. subtilis* FB17. Significant increase in total biomass was observed in *O. sativa* (rice; cultivar Nipponbare) (over 200%) post FB17 treatment.

FIG. 21 illustrates aerial & root biomass increase in rice plants, *Oryza sativa* (Nipponbare), treated with *B. subtilis* FB17 60 days after inoculation. Overnight cultures of FB17 grown in LB were used to generate an inoculum of $10^8$ cells per ml. Four week old hydroponically grown rice plants (cultivar Nipponbare) were used for FB17 supplementation. The rice plants that were administered *B. subtilis* FB17 exhibited an increase of about 200% biomass compared to untreated rice plants.

Example 8

To evaluate if *Bacillus subtilis* FB17 colonizes rice roots, rice plants (cultivar Nipponbare) were inoculated with *Bacillus subtilis* FB17 and the roots of the rice plants were observed 96 hrs post-inoculation by confocal scanning laser microscopy. Observations confirmed that the beneficial rhizobacteria (*Bacillus subtilis* FB17) form biofilm in planta. In particular, the data suggest that *Bacillus subtilis* FB17 efficiently colonizes the rice roots post 96 hrs of treatment, indicating that rice roots support the colonization of beneficial microbes.

To evaluate if rhizobacterial treatment of rice plants inflicts any changes in stomatal aperture, applicants analyzed rice plants treated with rhizobacteria. Results showed that rhizobacterial treatment of rice with *Bacillus subtilis* FB17 greatly reduced the stomatal aperture in treated rice plants (cultivar Nipponbare). In the case of *Bacillus subtilis* FB17 treatment, guard cells were observed 1 week after addition of *Bacillus subtilis* FB17. These results suggest that *B. subtilis* FB17 (*Bacillus subtilis* FB17) inflicts a general stomatal closure response in both monocots and dicot plants as evidenced with both *A. thaliana* and rice.

To evaluate if *Bacillus subtilis* FB17 attenuates the growth of rice blast, applicants exposed *Magnaporthe oryzae* to *Bacillus subtilis* FB17 cultures. Qualitative compartment plates and quantitative data showed that *Bacillus subtilis* FB17 attenuated the growth of *M. oryzae* as shown by reduced radial growth in the *Bacillus subtilis* FB17 exposed fungal cultures. Comparison with the controls (TY & LB) demonstrates the extent to which the pathogen would grow with no treatment. As shown in Table 1, *Bacillus subtilis* FB17 restricted *M. oryzae*'s growth by about 25% in vitro. These results suggest that *B. subtilis* FB17 produces an antifungal volatile compound which may attenuate or inhibit *M. oryzae*'s growth.

TABLE 1

| Treatment | Fungal colony avg. diameter (cm) | Percent fungal growth relative to control treatment |
|---|---|---|
| TY control | 3.175 | 100 |
| LB control | 3.098 | 100 |
| *Bacillus subtilis* FB17 | 2.342 | 75.59 |

*Bacillus subtilis* FB17 induced systemic resistance in rice and barley to *Magnaporthe oryzae*. Both rice and barley plants that were exposed to *M. oryzae* had reduced lesion formation on rice leaves and barley cotyledons, respectively, in FB17-treated plants compared to controls, as shown in Table 2 ("infected" was defined as a leaf having as least one typical diamond-shaped Blast lesion on it).

TABLE 2

| | # infected leaves | Total # lesions |
|---|---|---|
| None/Mo | 3 | 23 |
| FB17/Mo | 5 | 13 |

Example 9

To evaluate if *Bacillus subtilis* FB17 increases iron fortification in rice, the applicants analyzed the overall iron content in rice leaves, roots, and grains in plants supplemented with *Bacillus subtilis* FB17, using inductively coupled plasma-atomic emission spectroscopy (ICP-AES). Results showed that *Bacillus subtilis* FB17 supplementation to rice helps mobilize iron in planta, i.e., the essential element iron is actively taken up by the plant where it is utilized for plant growth and development. As illustrated in FIG. 22, an 81% increase in iron content was observed in FB17-treated rice plants compared to untreated control, as measured by mg of iron per kg of dry weight of the plant ("UD1022," as stated in FIG. 1 refers to *Bacillus subtilis* FB17). Thus, administration of *Bacillus subtilis* FB17 to plants, particularly rice plants, can greatly enhance the nutritional value of food by increasing iron concentrations in the food.

FIG. 23 summarizes the effects of *B. subtilis* FB17 on different traits in multiple plant species described above.

Although the present invention has been described in connection with specific embodiments, it should be understood that the invention as claimed should not be unduly limited to such specific embodiments. Indeed, various modifications and variations of the described compositions and methods of the invention will be apparent to those of ordinary skill in the art and are intended to be within the scope of the appended claims.

What is claimed is:

1. A method for enhancing a characteristic of a plant, the method comprising administering a composition comprising *Bacillus subtilis* FB17 to seed of a plant in an amount effective to produce an enhanced characteristic in the plant grown from the seed compared to the seed not treated with the composition comprising *Bacillus subtilis* FB17, wherein the enhanced characteristic comprises greater biomass, greater drought tolerance, decreased lignin content, increased rate of seed germination, increased iron concentration, increased tolerance to pathogens, or any combination thereof.

2. The method of claim 1, wherein the plant is selected from the group consisting of a monocot plant or a dicot plant.

3. The method of claim 2, wherein the monocot plant is a cereal plant.

4. The method of claim 3, wherein the cereal plant is a corn plant, a barley plant, or a rice plant.

5. The method of claim 2, wherein the dicot plant is a soybean plant or a tomato plant.

6. The method of claim 1, wherein the plant is a bioenergy crop plant.

7. The method of claim 6, wherein the plant is *Brachypodium distachyon*.

8. The method of claim 1, comprising administering the *Bacillus subtilis* FB17 composition in an amount effective to produce a greater biomass in the plant grown from the seed by about 5% to about 100% compared to a plant grown from an untreated seed.

9. The method of claim 1, comprising administering the *Bacillus subtilis* FB17 composition to the seed in an effective amount up to about $1 \times 10^8$ CFU/seed.

10. The method of claim 1, comprising administering the *Bacillus subtilis* FB17 composition to the seed of the plant prior to planting or with the seed at planting.

11. A method for coating plant seed for enhancing a characteristic of a plant grown from the seed, the method comprising treating seed of a plant with a composition comprising *Bacillus subtilis* FB17 in an amount effective to produce an enhanced characteristic in the plant grown from the treated seed compared to a plant grown from the seed not treated with the composition comprising *Bacillus subtilis* FB17, wherein the enhanced characteristic comprises greater biomass, greater drought tolerance, decreased lignin content, increased rate of seed germination, increased iron concentration, increased tolerance to pathogens, or any combination thereof.

12. The method of claim 11, wherein the plant is selected from the group consisting of a monocot plant or a dicot plant.

13. The method of claim 12, wherein the monocot plant is a cereal plant.

14. The method of claim 13, wherein the cereal plant is a corn plant, a barley plant, or a rice plant.

15. The method of claim 12, wherein the dicot plant is a soybean plant.

16. A method for producing a biofuel, said method comprising converting the biomass of the plant of claim 1 to said biofuel, which plant has been grown from seed administered with the *Bacillus subtilis* FB17 composition.

17. The method of claim 14, wherein the plant is a rice plant.

18. The method of claim 17, comprising administering the *Bacillus subtilis* FB17 composition in an amount effective to produce a greater iron concentration in the rice plant grown from seed by at least about 25% compared to a rice plant grown from an untreated seed.

19. The method of claim 1, comprising administering *Bacillus subtilis* FB17 composition to the seed of the plant in an amount effective to inhibit infection of the plant by a fungal pathogen compared to a plant from an untreated seed.

20. The method of claim 19, wherein the plant is a rice plant and the fungal pathogen is rice blast.

21. The method of claim 20, comprising administering the *Bacillus subtilis* FB17 composition to the seed of the rice plant prior to planting or with the seed at planting.

22. The method of claim 20, wherein symptoms of the rice blast are reduced by about 5% to about 100% compared to an untreated plant.

23. A plant seed coating comprising *Bacillus subtilis* FB17 in an amount effective to produce an enhanced characteristic in a plant grown from a seed treated with the plant seed coating compared to the seed not treated with the composition comprising *Bacillus subtilis* FB17, wherein the enhanced characteristic comprises greater biomass, greater drought tolerance, decreased lignin content, increased rate of seed germination, increased iron concentration, increased tolerance to pathogens, or any combination thereof.

24. A plant seed comprising the coating of claim 23.

* * * * *